US008439921B2

(12) United States Patent
Jamali

(10) Patent No.: US 8,439,921 B2
(45) Date of Patent: May 14, 2013

(54) DEVICE AND METHOD FOR ALLOGRAFT TOTAL HIP ARTHROPLASTY

(76) Inventor: Amir Jamali, Sacramento, CA (US)

( * ) Notice: Subject to any disclaimer, the term of this patent is extended or adjusted under 35 U.S.C. 154(b) by 253 days.

(21) Appl. No.: 12/370,486

(22) Filed: Feb. 12, 2009

(65) Prior Publication Data
US 2009/0209963 A1 Aug. 20, 2009

Related U.S. Application Data

(60) Provisional application No. 61/028,154, filed on Feb. 12, 2008.

(51) Int. Cl.
*A61B 17/00* (2006.01)
(52) U.S. Cl.
USPC ............. 606/81; 606/79; 606/80; 606/86 R; 606/89
(58) Field of Classification Search ............ 606/79–85, 606/86 R, 89, 91, 99; 623/18.11, 20.35, 22.11, 623/22.12, 22.15, 22.17–22.34
See application file for complete search history.

(56) References Cited

U.S. PATENT DOCUMENTS

| | | |
|---|---|---|
| 3,686,922 A | 8/1972 | Bley |
| 3,741,706 A | 6/1973 | Conley |
| 4,904,265 A | 2/1990 | MacCollum |
| 5,176,711 A | 1/1993 | Grimes |
| 5,320,626 A | 6/1994 | Schmieding |
| 5,329,846 A | 7/1994 | Bonutti |
| 5,423,823 A | 6/1995 | Schmieding |
| 5,514,141 A * | 5/1996 | Prizzi, Jr. ............. 606/80 |
| 5,540,692 A * | 7/1996 | Tidwell .............. 606/79 |
| 5,713,374 A | 2/1998 | Pachence |
| 5,782,835 A | 7/1998 | Hart et al. |
| 5,824,078 A | 10/1998 | Nelson et al. |
| 5,919,196 A | 7/1999 | Bobic et al. |
| 6,156,069 A | 12/2000 | Amstutz |
| 6,358,253 B1 | 3/2002 | Torrie |
| 6,458,161 B1 | 10/2002 | Gibbs |
| 6,488,033 B1 | 12/2002 | Cerundolo |
| 6,591,581 B2 | 7/2003 | Schmieding |
| 6,595,999 B2 | 7/2003 | Marchione et al. |
| 6,602,258 B1 * | 8/2003 | Katz ................. 606/80 |
| 7,160,305 B2 | 1/2007 | Schmieding |
| 7,241,315 B2 | 7/2007 | Evans |
| 7,264,634 B2 | 9/2007 | Schmieding |
| 2003/0130741 A1 | 7/2003 | McMinn |
| 2003/3018751 | 10/2003 | McMinn |
| 2004/0199258 A1* | 10/2004 | Macara ............. 623/22.32 |
| 2007/0135918 A1 | 6/2007 | Malinin |
| 2007/0162038 A1 | 7/2007 | Tuke |
| 2007/0276393 A1* | 11/2007 | Bonadei ............. 606/80 |
| 2007/0299451 A1* | 12/2007 | Tulkis ............. 606/79 |

OTHER PUBLICATIONS

Bugbee, W., "Fresh Osteochondral Allografts." Semin Arthroplasty 11.4 (2000): 1-7.

(Continued)

*Primary Examiner* — Andrew Yang
*Assistant Examiner* — Olivia C Chang
(74) *Attorney, Agent, or Firm* — Craig M. Stainbrook; Stainbrook & Stainbrook, LLP

(57) ABSTRACT

Method and apparatus for preparing bone and cartilage transplants for the reconstruction of the acetabulum, femoral head, or both with tissue engineered osteochondral constructs or and osteochondral allograft transplant.

9 Claims, 26 Drawing Sheets

OTHER PUBLICATIONS

Bugbee, W.D. and Convery, F.R. "Osteochondral Allograft Transplantation." ClinSports Med 18.1 (1999): 67-75.

Bugbee, W.D., et al. "Fresh Osteochondral Allografting of the Patellofemoral Joint." Proceedings of the 69th Annual Meeting of the American Academy of Arthopaedic Surgeons. San Francisco, CA, 2001.

Emmerson, B.C., et al. "Fresh Osteochondral allografting in the Treatment of Osteochondritis Dissecans of the Femoral Condyle." American Journal of Sports Medicine 35.6 (2007): 907-14.

Jamali, A.A. et al. "Fresh Ostechondral Allografts: Results in the Patellofemoral Joint." Clin Orthop Relat Res. 437 (2005): 176-85.

Jamali, A.A.; Hatcher, S.L.; and You, Z. "Donor Cell Survival in a Fresh Osteochondral Allograft at Twenty-Nine Years. A Case Report." J Bone Joint Surg Am 39.1 (2007): 166-9.

Meyers, M.H. "Resurfacing of the Femoral Head with Fresh Osteochondral Allografts. Long Term Results." Clin Ortop. 197 (1985): 111-4.

Allograft OATS surgical technique. Arthrex.

McMinn, D. "Smith & Nephew Birmingham Hip Resurfacing Surgical Technique"; Booklet dated Apr. 2006, Smith & Nephew, Memphis, TN, USA, 36 pgs.

* cited by examiner

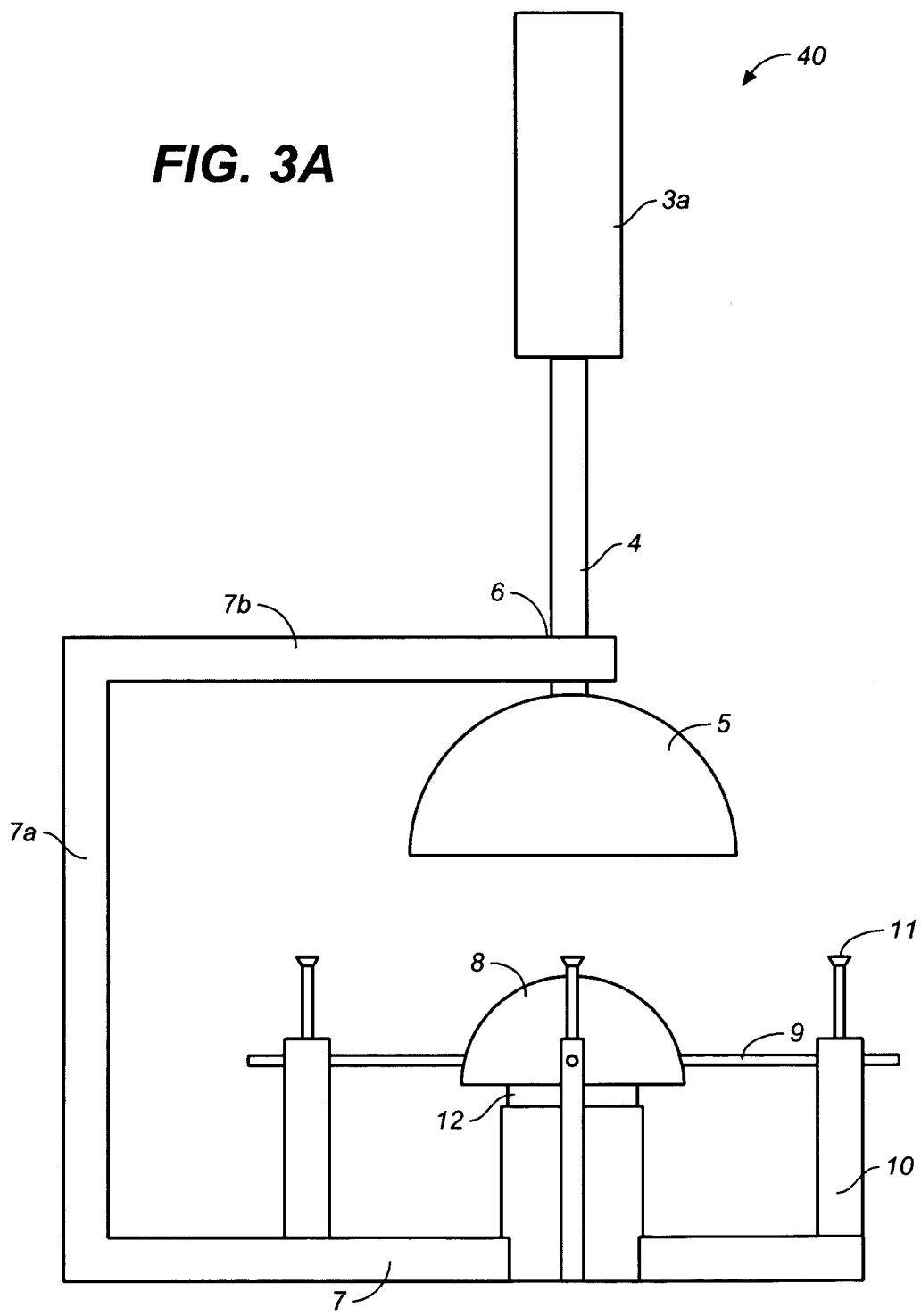

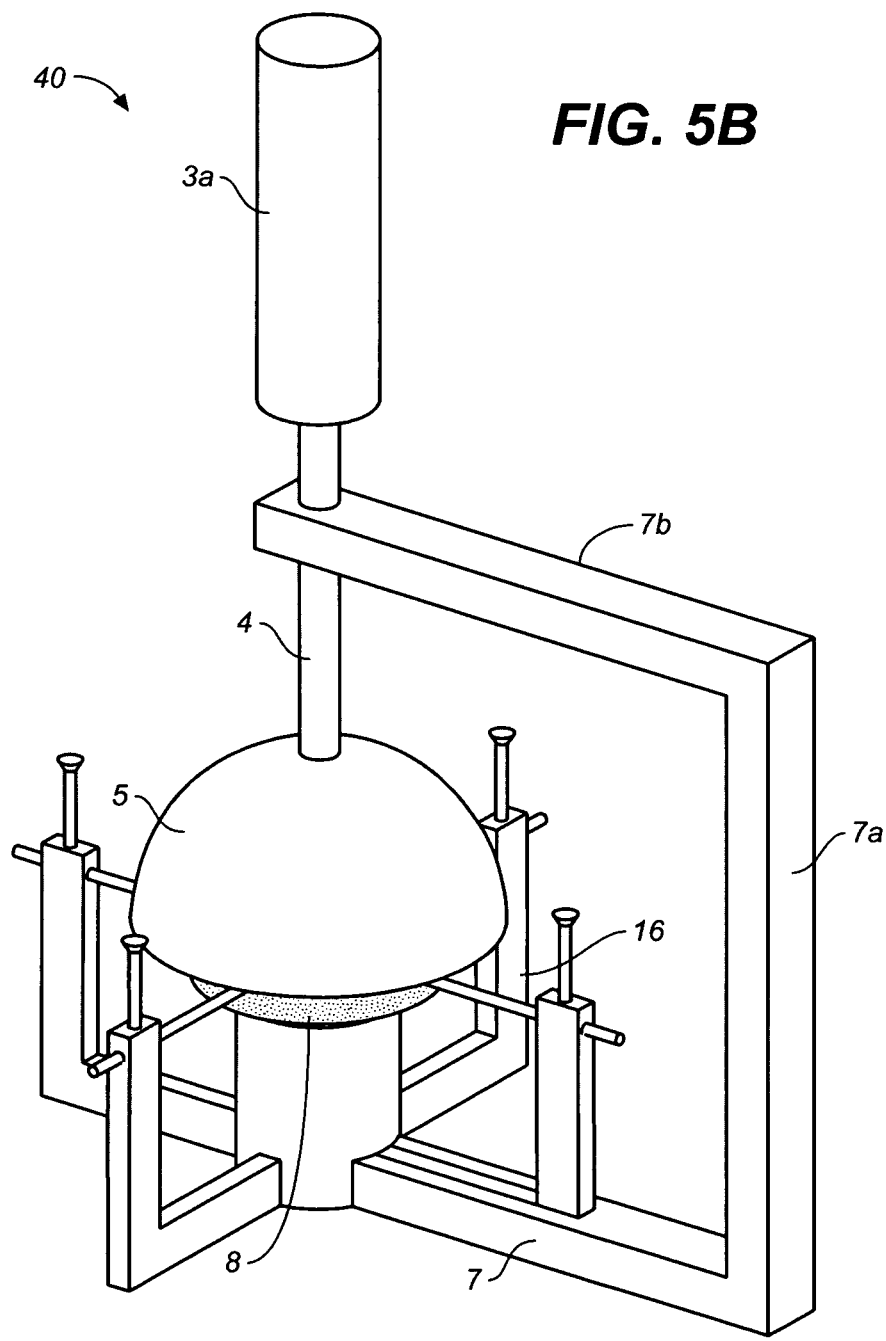

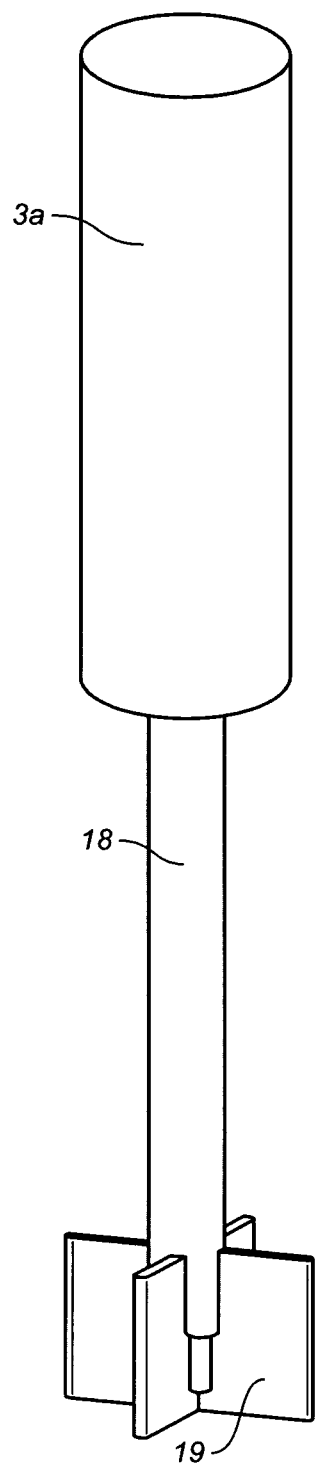 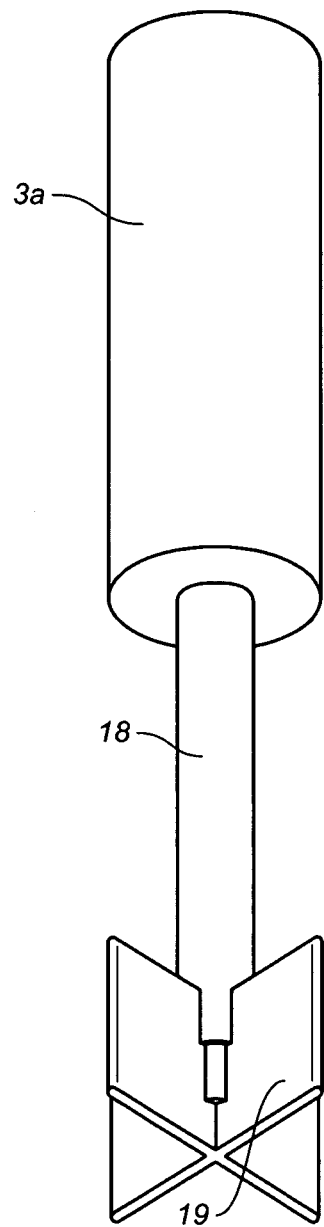
*FIG. 7A*  *FIG. 7B*

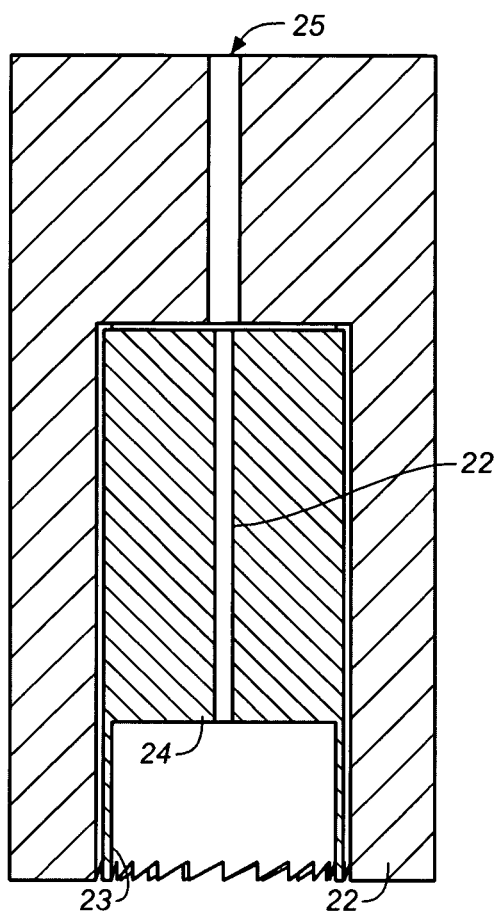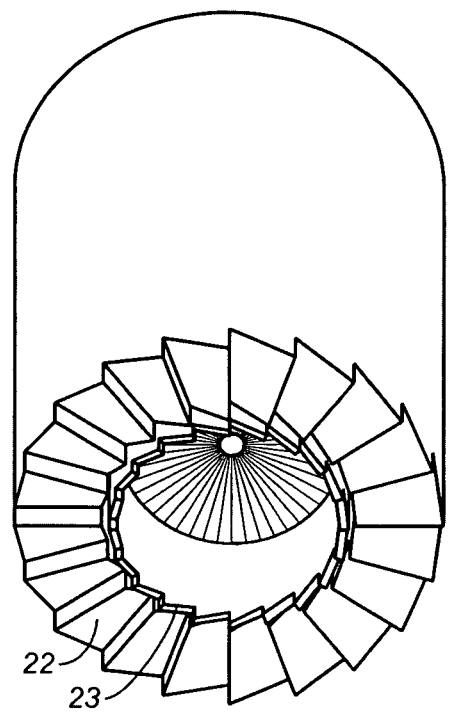
*FIG. 13A*  *FIG. 13B*

DEVICE AND METHOD FOR ALLOGRAFT TOTAL HIP ARTHROPLASTY

CROSS REFERENCES TO RELATED APPLICATIONS

The present application claims the benefit of U.S. Provisional Patent Application Ser. No. 61/028,154, filed Feb. 12, 2008.

SEQUENCE LISTING

Not applicable.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates generally to the preparation of bone and cartilage transplants for reconstruction of the acetabulum, femoral head, or both, using tissue engineered osteochondral constructs and/or an osteochondral allograft transplant.

2. Discussion of Related Art Including Information Disclosed Under 37 CFR §§1.97, 1.98

The reconstruction of human joints is an area of ongoing investigation. Since the work of Erich Lexer in the early part of the twentieth century, entire joints have been transplanted into human patients. These large grafts, termed "allografts," were initially associated with high failure rates and cartilage degeneration. Additionally, patients were required to immobilize and avoid bearing weight on the treated joint for long periods.

In the early 1970's, the concept of shell allografts of fresh bone and cartilage was introduced. With these grafts, only a thin shell of bone was transplanted, in essence as a carrying vehicle for the fresh articular cartilage which would remain populated with cells from the donor. Once the bone of the host healed to the graft bone, the articular cartilage would continue to receive its nutrition from the synovial fluid in the joint. The bone, due to its small volume, generated a minimal immune response. Using this technique, large areas of articular cartilage could be repaired with normal cartilage without the need for systemic immunosuppressive medications. The success of this surgical procedure has been documented based on both clinical improvements as well as documented long-term donor cell viability for nearly 30 years after the transplantation.

In the area of instrumentation for fresh osteochondral allografts, current preparation systems are almost universally based on the preparation of cylindrical cores that can be trimmed and transplanted into matched cylindrically prepared recipient sites in the complementary position of the joint. In U.S. Pat. No. 6,488,033, Cerundolo describe obtaining and placing an osteochondral allograft in the same location of the joint and in the same orientation to optimize the surface matching of the graft surface to the native joint. However, this invention does not shed any light or provide any solution to the challenges in performing a total joint allograft on a ball and socket joint such as the hip, nor does this invention discuss any automated jig for achieving precise orientation in the preparation of the grafts. Schmieding presents a method and instrumentation for the preparation, distribution, and insertion of round, size specific osteochondral allografts in U.S. Pat. No. 6,591,581. In this document, the distribution network for fresh osteochondral allografts is laid out, along with details for instrumentation in preparing such osteochondral plugs and recipient sites. This instrumentation is analogous to that discussed in U.S. Pat. No. 5,919,196 for autologous osteochondral transfer, otherwise known as mosaicplasty. However, no insights are offered into the challenges of preparing an osteochondral allograft total hip replacement.

In spite of the success in multiple anatomical areas, the use of fresh osteochondral allografts in the hip joint had been limited by the architectural constraints of this joint and the lack of a technique for preparation of grafts to allow for a uniform thickness and architecture. Up to now, the only treatment for replacement of the entire hip joint has been total joint arthroplasty with metal, ceramic and/or polyethylene implants. There are a number of limitations with these options particularly in the very young patient with hip disease. The longevity of traditional hip replacements has been limited by a phenomenon known as osteolysis, whereby debris, usually from the polyethylene bearing, is deposited along the prosthesis and leads to a cellular cascade leading to digestion of the bone and loss of its mechanical integrity, ultimately leading to loosening with large cavitary defects in the bone. Newer technology has become available over the past ten years including the cross linking of polyethylene, the use of ceramic on ceramic bearings, and the resurgence of metal on metal bearings. Each of these has the potential to decrease long-term debris generated bone lysis and implant loosening. An additional disadvantage of standard hip replacements is the mandatory removal of the entire femoral head and passage of a stem into the medullary canal of the femur. This ultimately leads to decreased loading of the proximal femur and the loss of bone density known as stress-shielding. Recently, there has been a resurgence of interest in a procedure known as total hip resurfacing arthroplasty otherwise known as hip resurfacing. With this technique the femoral head is reshaped but preserved and a metal cap is placed on the head usually using bone cement, in effect recapping the femoral head. The resurgence of hip resurfacing has been made possible with improved metal alloy preparation with improved tolerances between the femoral and acetabular components and improved alloy hardness. With this new technology, metal sockets have become available allowing resurfacing of both sides of the joint to make total hip resurfacing a reality. In spite of the benefits of a head preserving operation, total hip resurfacing is associated with high urine and blood metal ion levels as well as risk of complications such as loosening, avascular necrosis, and femoral neck fracture. Additionally, since metal implants are utilized the joint is placed at risk for future revision arthroplasties. Based on the current state of the art in joint arthroplasty, a need for a biological method for restoration of hyaline articular cartilage in the hip is required.

BRIEF SUMMARY OF THE INVENTION

To address the needs set out above, the present invention is a specialized device for the preparation of the graft acetabular bone and femoral head bone for implantation of a total hip allograft replacement. A tower is utilized to precisely prepare the outer surface of the acetabulum to a thickness of between 5 mm and 10 mm thick in a uniform fashion with concurrent preparation of a donor femoral head for resurfacing of the femur with a matching graft, thus performing a biological total hip arthroplasty.

As an alternative embodiment, the recipient femoral head can be managed with an off the shelf resurfacing metal or ceramic prosthetic femoral component which rests on the prepared surface of the head and neck. The resurfacing implant embodied in this invention differs from previous resurfacing implants based on the presence of a circumferential perpendicular support of the implant at the periphery of the head. Traditional resurfacing femoral implants such as the Birmingham Resurfacing System or that disclosed in U.S. Pat. No. 6,156,069 by Amstutz are utilized with cylindrical preparation of the head in its entirety down to the concavity of the femoral neck. This resurfacing can be used in combination with the native cup as a hemiarthroplasty or partial joint replacement or in combination with a standard metal socket as is widely used by those skilled in the art of orthopaedic surgery.

Another embodiment of the present invention is the use of the allograft preparation system ("APS") in preparation of a tissue engineered osteochondral construct for implantation on the femoral head and with implantation of a complementary acetabular implantation in the pelvis. The techniques described above would be identical in preparation of the native bone beds for the tissue engineered joint in an identical fashion as described for the allograft transplant.

Other novel features characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention does not reside in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein:

FIG. 3A is a schematic side view in elevation of the allograft preparation system (APS) of the present invention, showing an acetabular harvester attachment;

FIG. 5B is the same view as that of FIG. 5A, but showing the harvester in a "down" position at or near the completion of reaming the outer surface of the graft FIG. 5A;

FIG. 7A is a schematic upper perspective view showing the femoral head graft reamer of the present invention, including the power source, the reamer shaft, and a cruciate reamer head;

FIG. 7B is a lower perspective view thereof;

FIG. 13A is a cross-sectional side view in elevation showing a cylindrical recipient inner femoral head reamer axially disposed in the opening of the outer cylindrical femoral head reamer;

FIG. 13B is a lower perspective view thereof;

DRAWING REFERENCE NUMERALS

FIGS. 1-3

Figure 1:
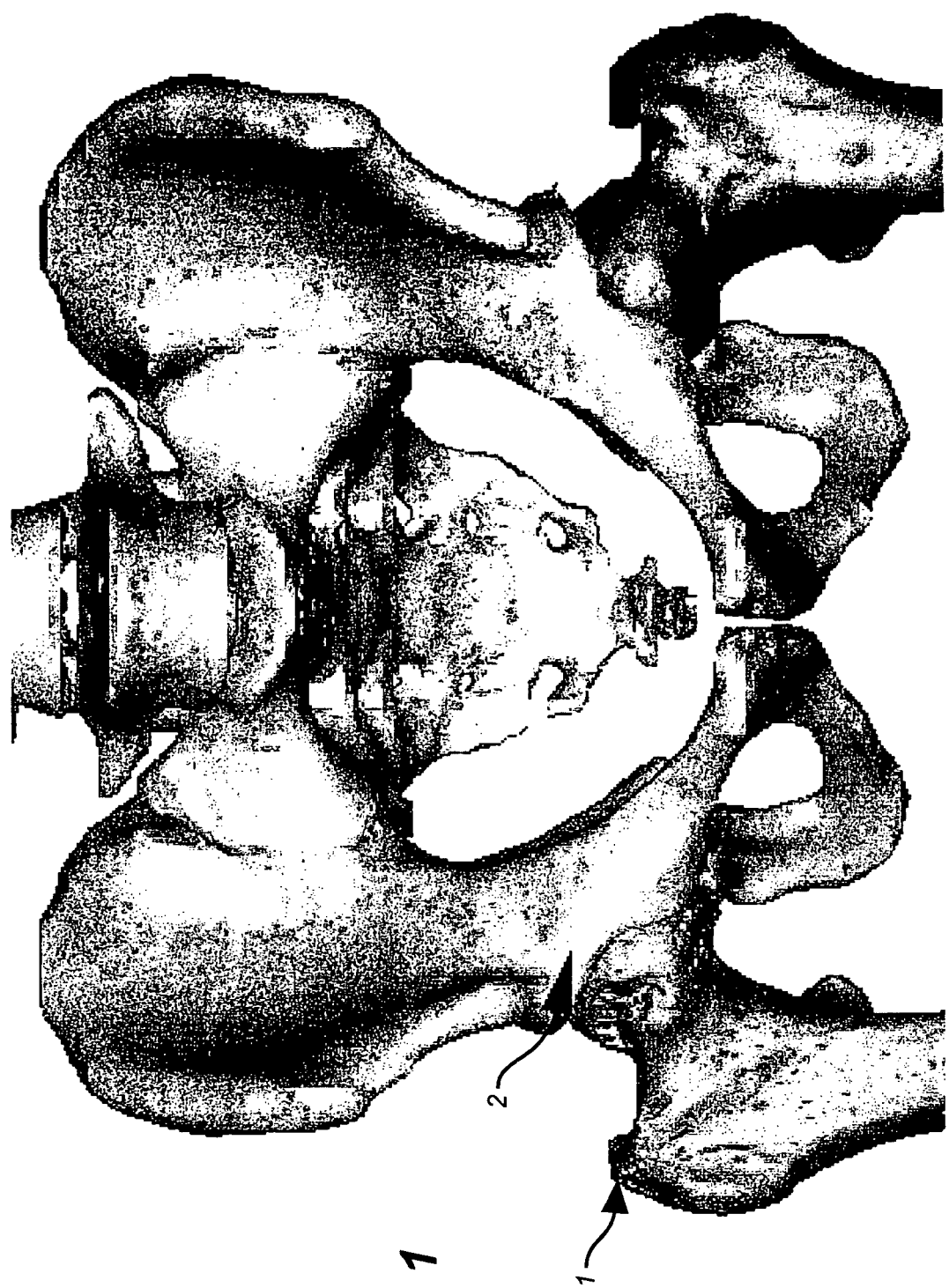
FIG. 1 is an anterior perspective view of the human pelvis and hip joints.

1 proximal femur
2 acetabulum or hip socket
3 allograft reamer
3a reamer driver
4 reamer shaft (drive shaft)
5 reverse hemispherical reamer
6 hole
7 base
7a vertical support
7b horizontal arm
8 acetabular platform
9 stabilization rods
10 stabilization towers
11 locking screws
12 pistons
40 acetabular preparation system (APS)

FIGS. 4-7A,B 13 ilium
14 pubis
15 ischium
16 acetabular graft (before reaming)
16a acetabular graft (after machining)
17 acetabular cavity
18 reamer shaft
19 cruciate head reamer
40 acetabular preparation system

FIGS. 8-10C 20 femoral head platform
21 allograft femoral head
40 acetabular preparation system

FIGS. 11A-13B 22 central cannulated aperture
23 inner reamer cutting blade
24 inner planing reamer surface
25 central cannulated aperture 26 inner cylindrical cavity
27 outer reamer cutting blade

FIGS. 14A-17

28 head
29 inner femoral head reamer
30 outer femoral head reamer
31 neck
32 femoral head
34 inner cavity
35 normalized periphery
36 implant
40 acetabular preparation system
42 guidepin

DETAILED DESCRIPTION OF THE INVENTION

The general anatomical structure of the human pelvis is shown schematically in FIG. 1. This view demonstrates the proximal femur 1 and the acetabulum or hip socket 2.

Figure 2:
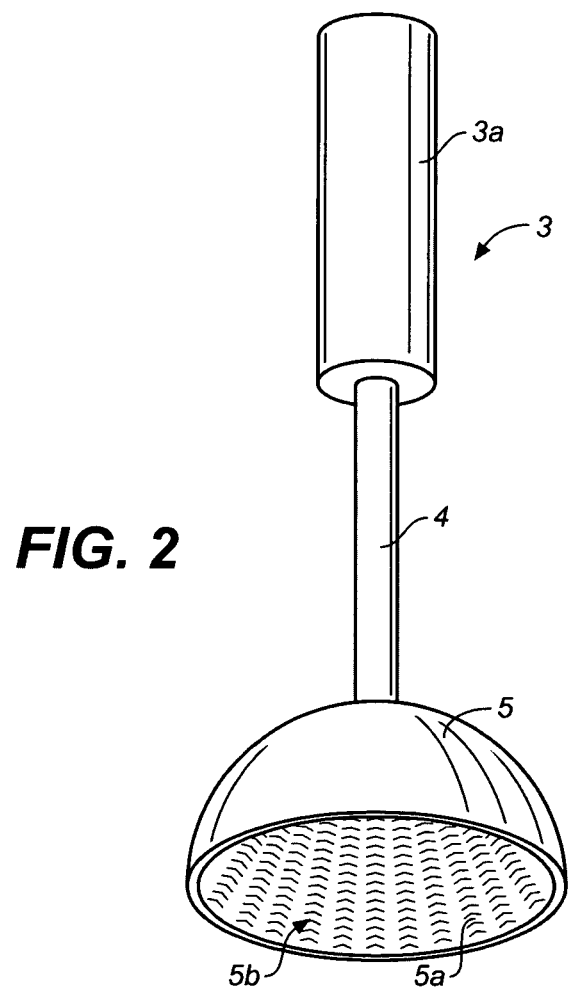
FIG. 2 is a lower perspective view showing a reverse hemispherical acetabular reamer.

FIG. 2 shows the acetabular allograft reamer 3 used in the harvesting of the graft acetabulum. This comprises a driver 3a, which can be pneumatic or electrical, depending on the available sources of power, a reamer drive shaft 4, and a cup-shaped, or reverse hemispherical, reamer 5. The reverse hemispherical reamer contains sharp gratings 5a on its downwardly facing inner surface 5b to remove excess bone and sculpt the acetabular graft to the precise size and thickness needed for the procedure.

Figure 3B:
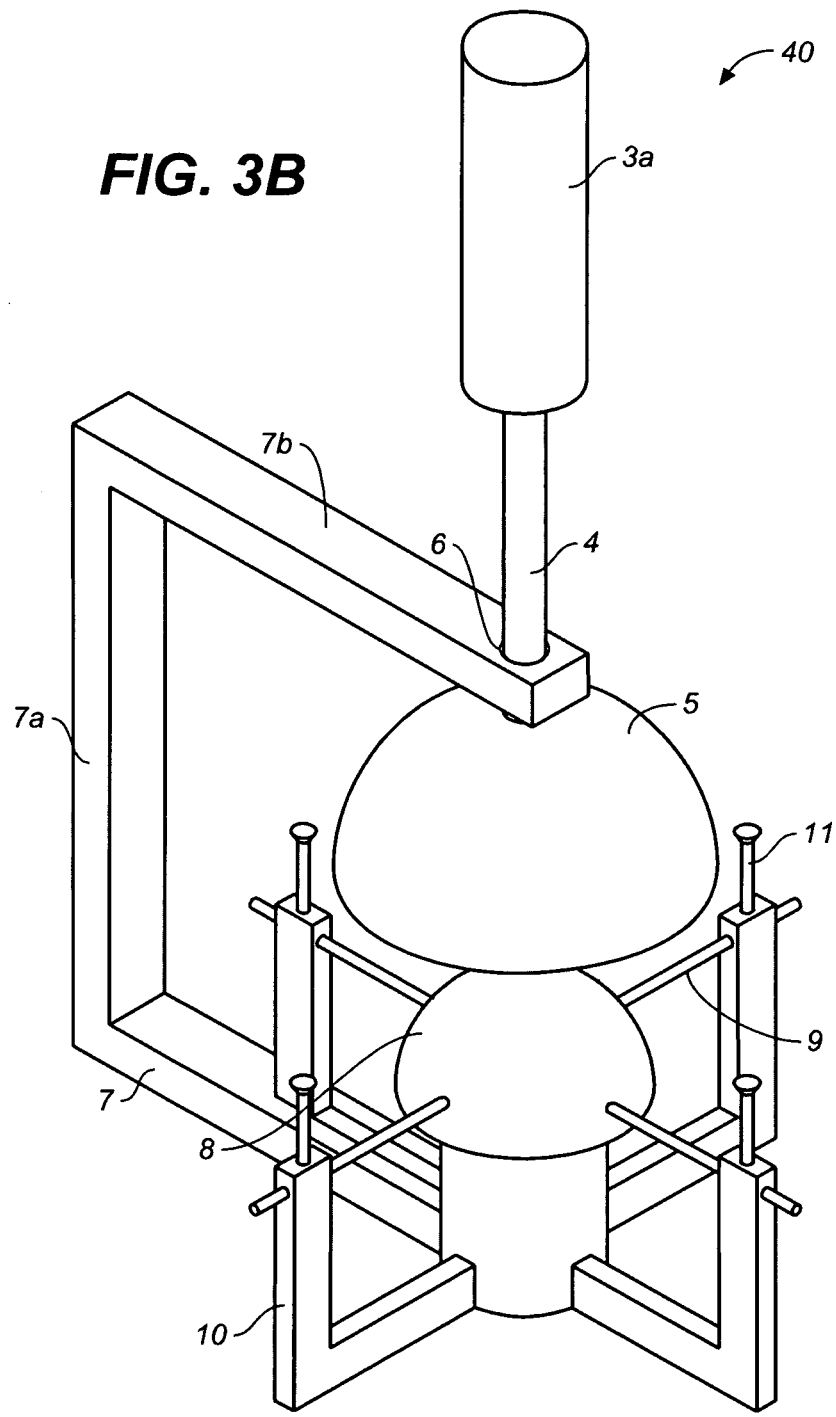
FIG. 3B is an upper front left view thereof.
Figure 3C:
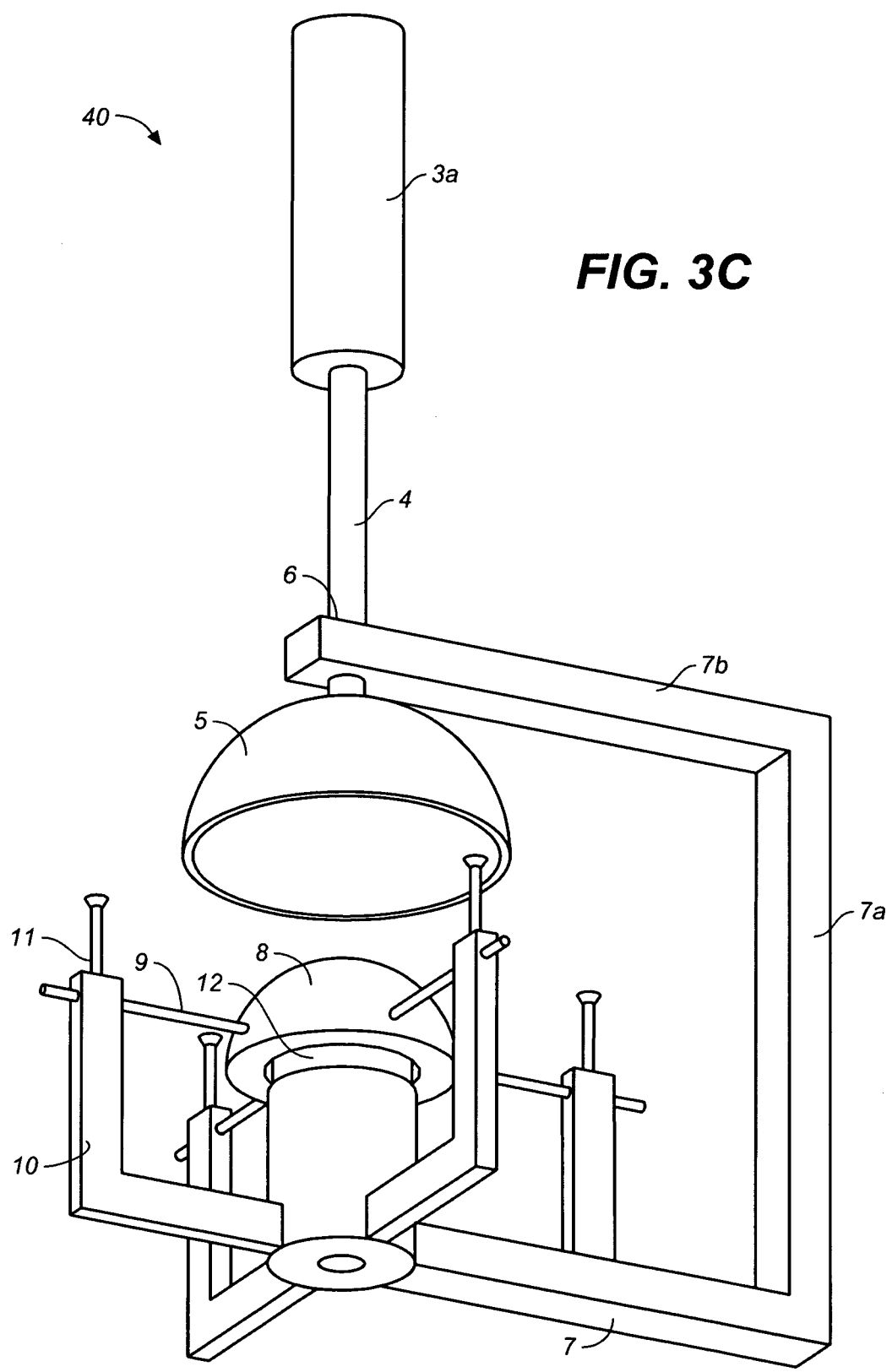
FIG. 3C is a lower front left view thereof.

FIGS. 3A-3C are schematic representations of the allograft preparation system (APS) 40 set up in acetabular mode. The APS, in the most essential terms, comprises a base 7 having a vertical support 7a with a horizontal arm 7b extending substantially parallel to the base, and thus to a surface on which the base may be disposed. In the acetabular mode, the reamer drive shaft 4 of an acetabular allograft reamer is inserted through a hole 6 in the horizontal arm 7b in order to mount the reamer in the APS. The hole in the horizontal arm is directly superior to an acetabular platform 8. The acetabular platform 8 is generally dome-shaped and is preferably selected from a set of interchangeable platforms having diameters varying from 36 mm up to 60 mm so as to accommodate different acetabular inner diameters for the allograft or tissue engineered acetabuli. The graft is placed onto the acetabular platform and achieves circumferential contact with the graft, clearly defining the inner dimensions of the acetabular graft as the graft is shaped from the outside in using a reverse hemispherical reamer 5. Workpiece holding apparatus, preferably metal stabilization rods 9 with sharp ends that can be either threaded or non-threaded, can be used to secure the graft during the reverse reaming process. The rods can thread into a threaded channel in vertically disposed stabilization towers 10 that extend upwardly from the base 7. They can be further stabilized using locking screws 11 at the superior aspect of the stabilization towers 10.

On the undersurface of the acetabular platform 8, a height-adjustable piston 12 is elevated or lowered to determine and fix the vertical position of the acetabular platform, the graft, and ultimately the polar thickness of the graft. The peripheral thickness of the graft is determined by the outer diameter of the reverse hemisphere acetabular reamer 5.

Figure 4:
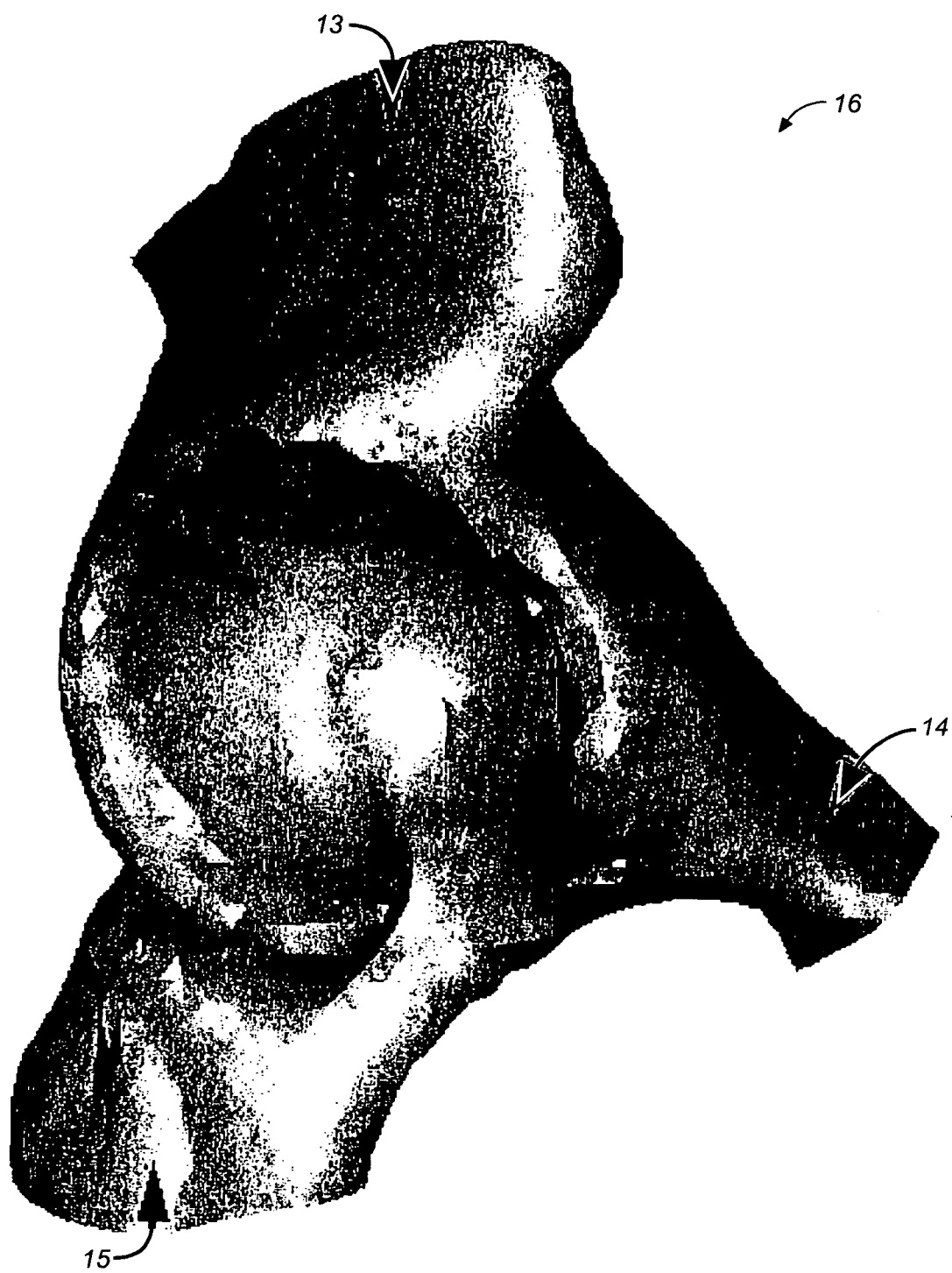
FIG. 4 is a schematic view of an acetabular graft after removal from donor with pubic, ischial, and iliac bony prominences.

FIG. 4 is a schematic representation of the acetabular graft 16 as it arrives in an unprepared form from the tissue bank. The graft demonstrates the three protrusions where it has been separated from the donor pelvis at the ilium 13, the pubis 14, and the ischium 15.

Figure 5A:
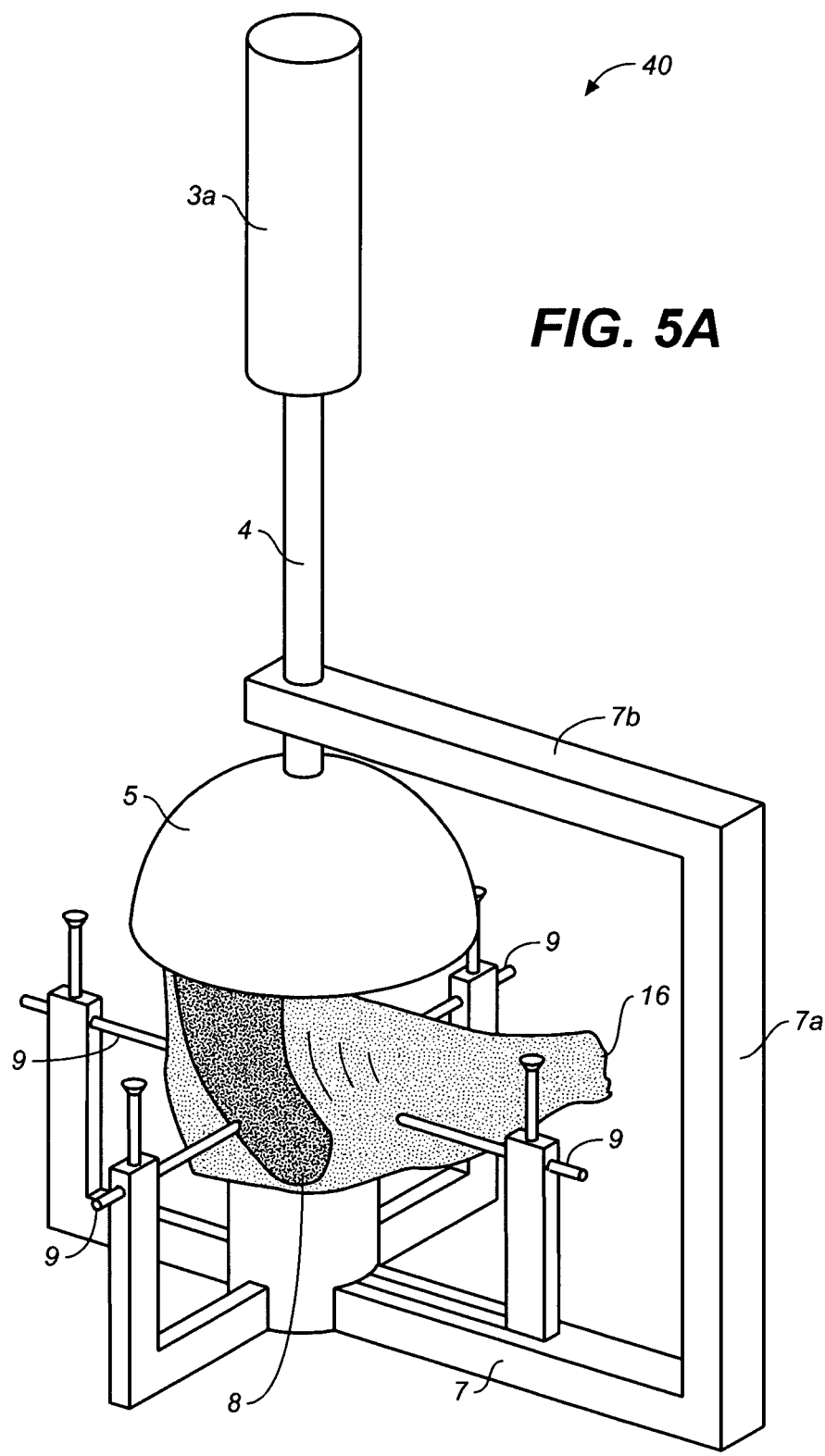
FIG. 5A is an upper right rear perspective view of an acetabular allograft placed in the APS of FIGS. 3A-3C, showing the harvester in an "up" position.
Figure 5C:
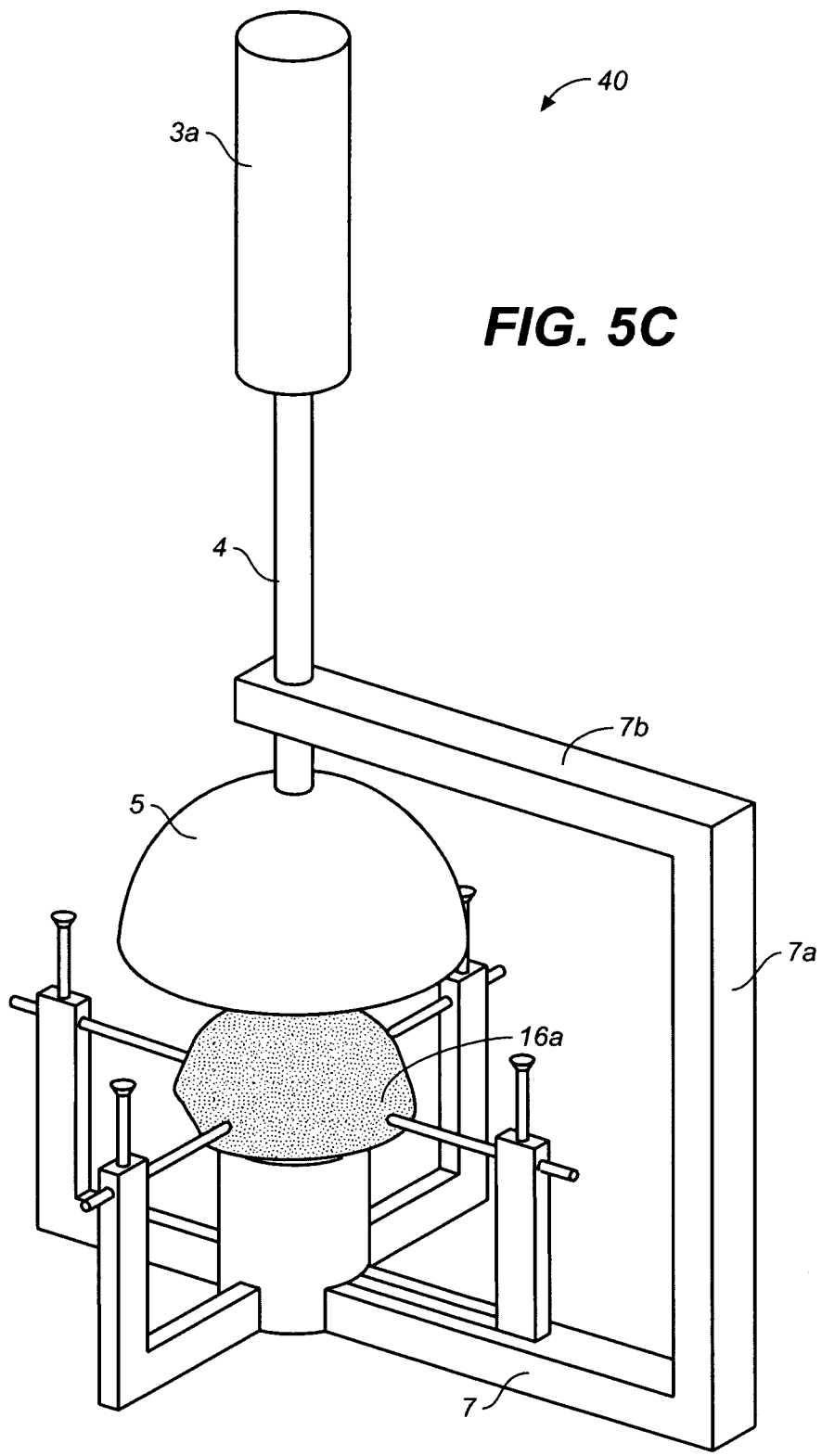
FIG. 5C is the same view as that of FIGS. 5A and 5B, but showing the harvester back in "up" position, thus demonstrating the hemispherical outer surface of the graft after reaming.

FIG. 5A-C, demonstrate the progression of steps used in preparation of the acetabular graft 16 from start to finish. In FIG. 5A, the acetabular graft has been placed in the APS with any residual prominent bony edges removed by the surgeon. In FIG. 5B, the reverse hemispherical reamer 5 is passed downward, and powered to precisely machine and contour the outer aspects of acetabular graft to a hemispherical shape. When the reamer is again raised to the up position, as shown in FIG. 5C, the prepared acetabular graft 16a is shown precisely sculpted into a hemisphere on its outer aspect.

Figure 6A:
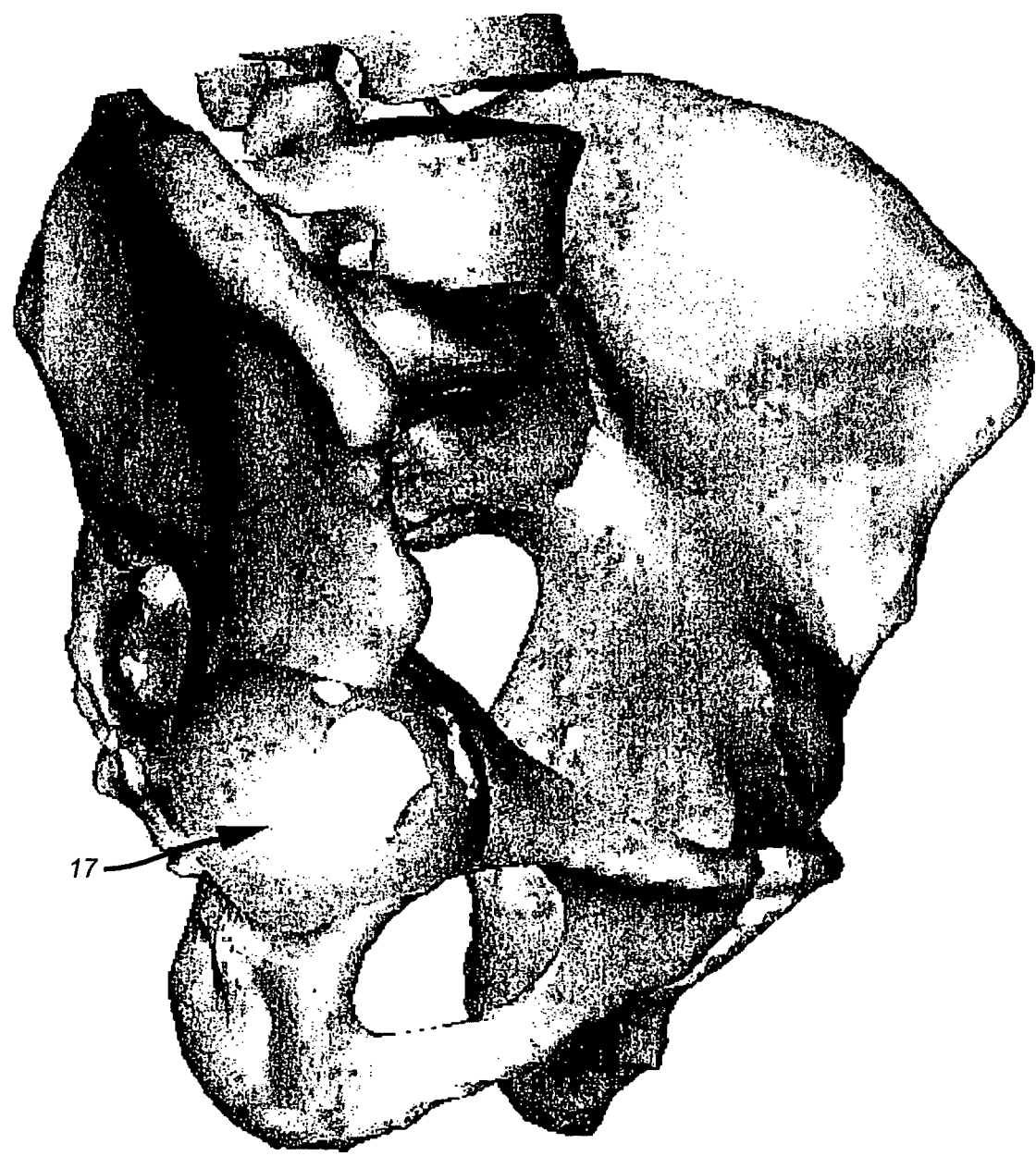
FIG. 6A is a schematic perspective view showing a recipient acetabulum after hemispherical reaming in a fashion similar to native total hip replacement.

In FIG. 6A, a schematic demonstration of the recipient's pelvis is shown. The diseased native acetabulum is removed by reaming with a standard hemispherical acetabular reamer used commonly by those skilled in the art of hip replacement surgery. The reaming is performed to between 0 mm and 2 mm under the size of the reverse hemispherical reamer used on the acetabular allograft. This forms a hemispherical acetabular cavity 17.

Figure 6B:
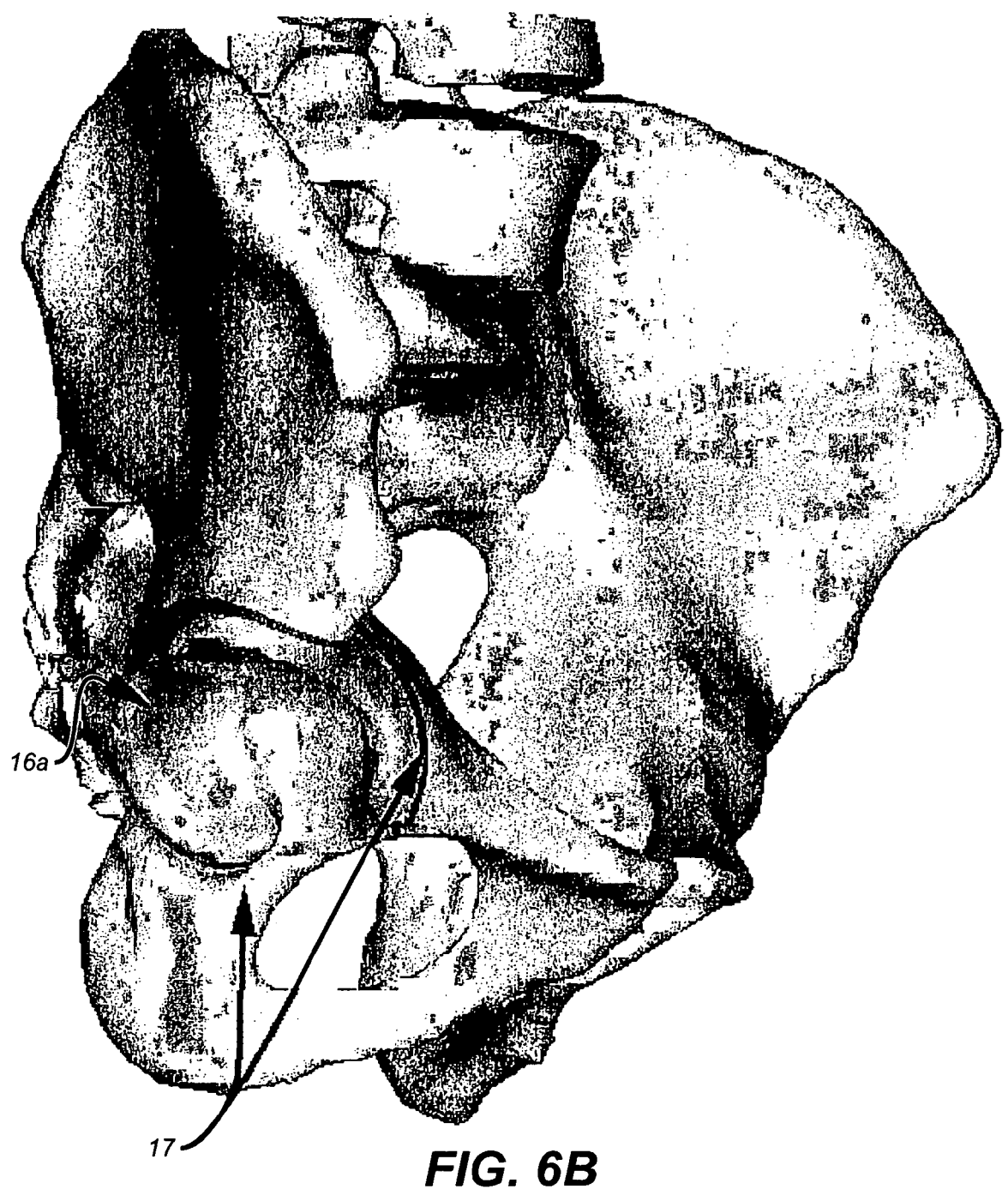
FIG. 6B is the same view as that of FIG. 6A, but showing placement of the prepared graft of FIG. 5C in the recipient acetabulum.

The prepared hemispherical acetabular allograft 16a is placed into the recipient defect 17 as seen in FIG. 6B, achieving intimate circumferential contact between the graft and the host bone.

Referring next to FIGS. 7A and 7B, there is shown a femoral head allograft reamer (which preferably utilizes the same driver 3a as that used in the acetabular allograft reamer), and which therefore comprises a driver operatively connected to a power source, a removable reamer shaft 18, and a cruciate head reamer 19. The cruciate reamer includes a plurality of blades, preferably from three to eight blades, and variable blade widths, with cutting edges perpendicular to the reamer drive shaft 18. The adjustable blade widths provide adjustments to the diameter of the final allograft femoral head cylindrical reamed cavity.

Figure 8:
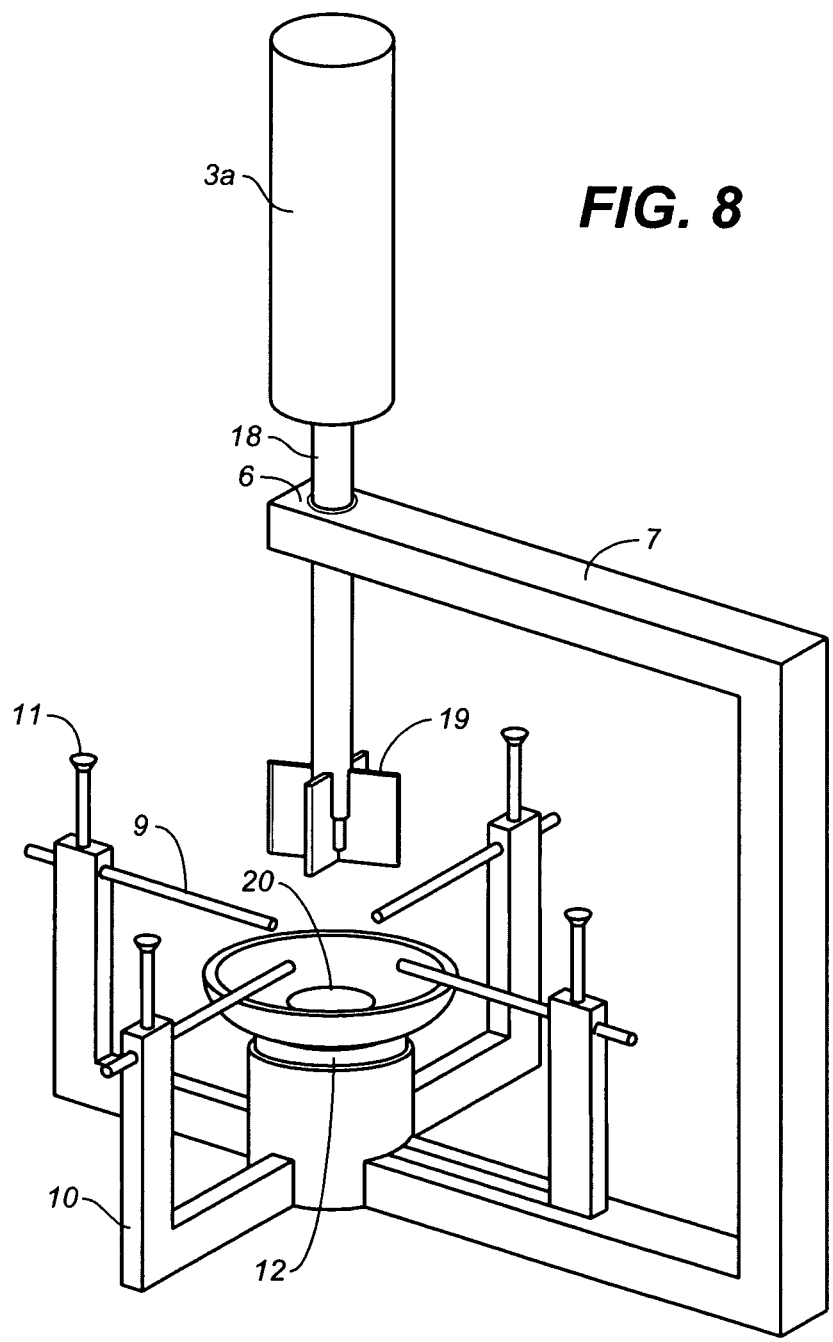
FIG. 8 is an upper right rear perspective view showing the APS assembly set up for harvesting a femoral head.

FIG. 8 shows the allograft preparation system (APS) in the femoral head preparation mode. The femoral head allograft reamer is mounted on the APS through a hole 6 in the horizontal arm of the APS 7. The hole in the horizontal arm is disposed immediately above, or directly superior to, the femoral head platform 20. The femoral head platform 20 is preferably cup-shaped and can be selected from a set of interchangeable platforms so as to have varying inner radii of curvature to accommodate various femoral head allograft sizes from 36 mm up to 60 mm. The femoral head graft is placed onto the platform and achieves circumferential contact with the femoral head platform. As seen previously in FIGS. 3A and 3B, metal stabilization rods 9 having sharp ends can be either threaded or non-threaded and employed to secure the femoral head at its peripheral surface during the cylindrical head reaming process. The rods can thread into a threaded channel in the stabilization towers 10. They can be further stabilized using locking screws 11 at the superior aspect of the stabilization towers 10. On the undersurface of the femoral head platform 20, a piston 12 with an interchangeable or adjustable height is used to determine the vertical position of the femoral head allograft and ultimately the polar thickness of the femoral head graft. The peripheral thickness of the graft is determined by the difference between the head diameter and the femoral head reamer diameter.

Figure 9A:
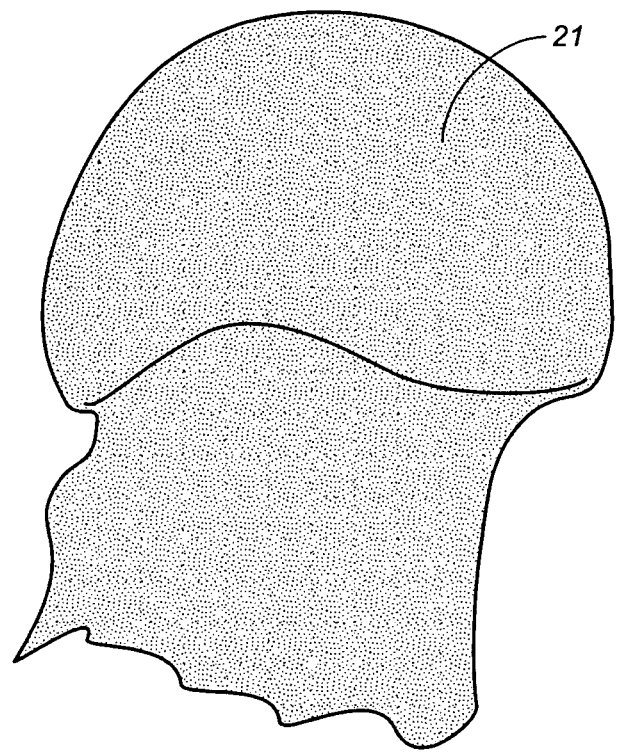
FIG. 9A is a schematic representation of a donor femoral allograft.
Figure 10C:
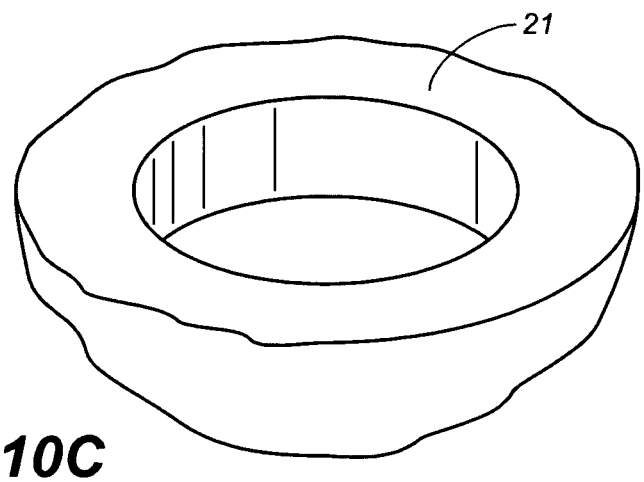
FIG. 10C is a lower perspective view showing the femoral head allograft after removal of the femoral neck and reaming by the femoral head reamer.
Figure 9B:
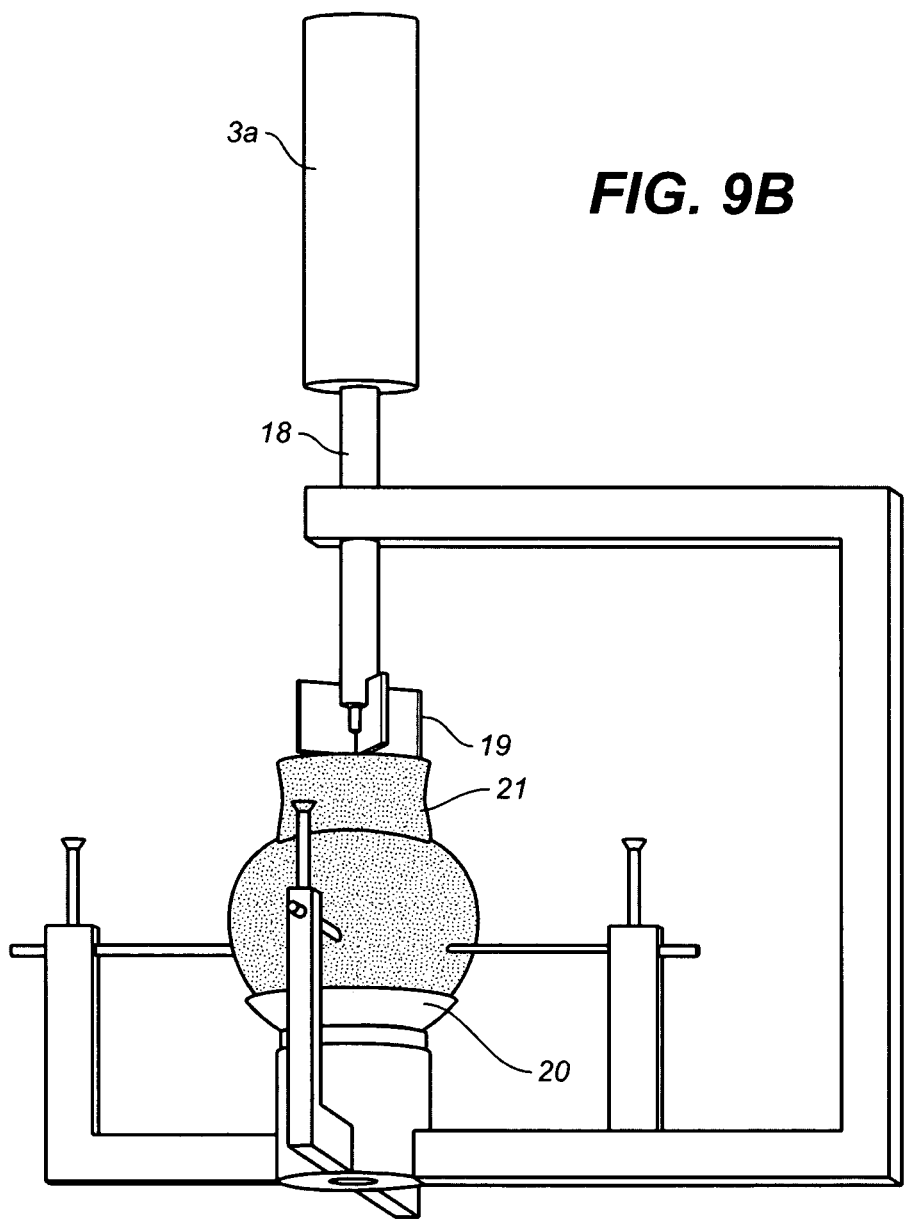
FIG. 9B is a lower right perspective view showing the femoral allograft of FIG. 9A placed in the APS with the reamer of the femoral head harvester setup poised immediately above the allograft in preparation for reaming.
Figure 10A:
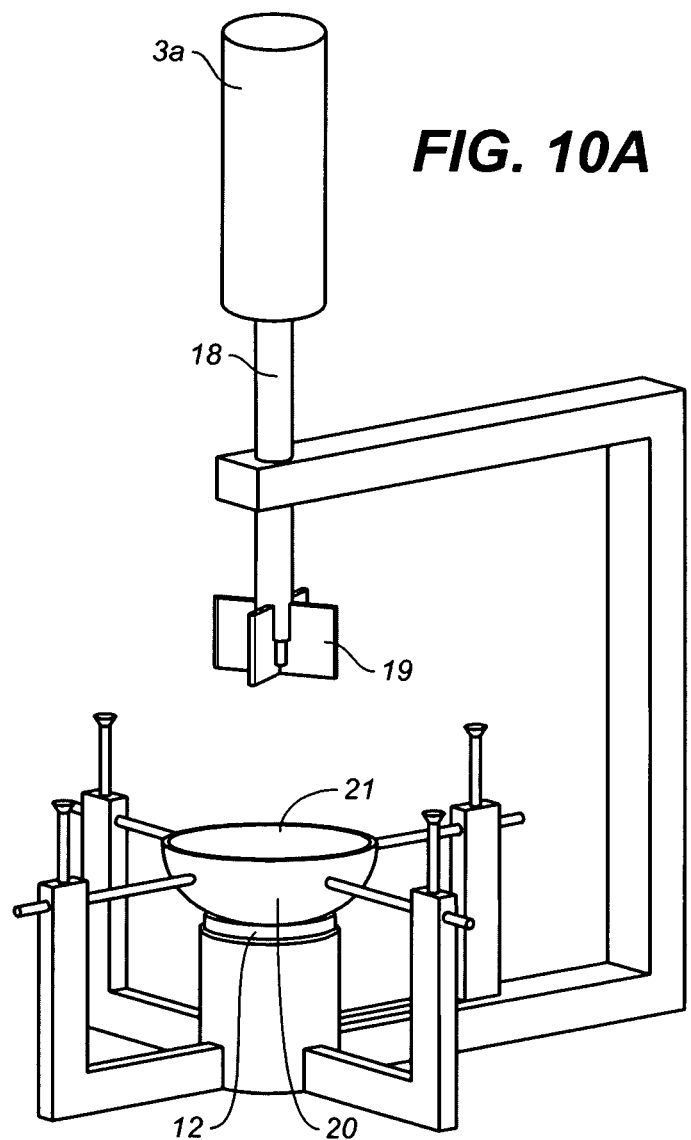
FIG. 10A is an upper front right perspective view of the femoral head harvester assembly of FIG. 8 showing the reamer in "up" position.
Figure 10B:
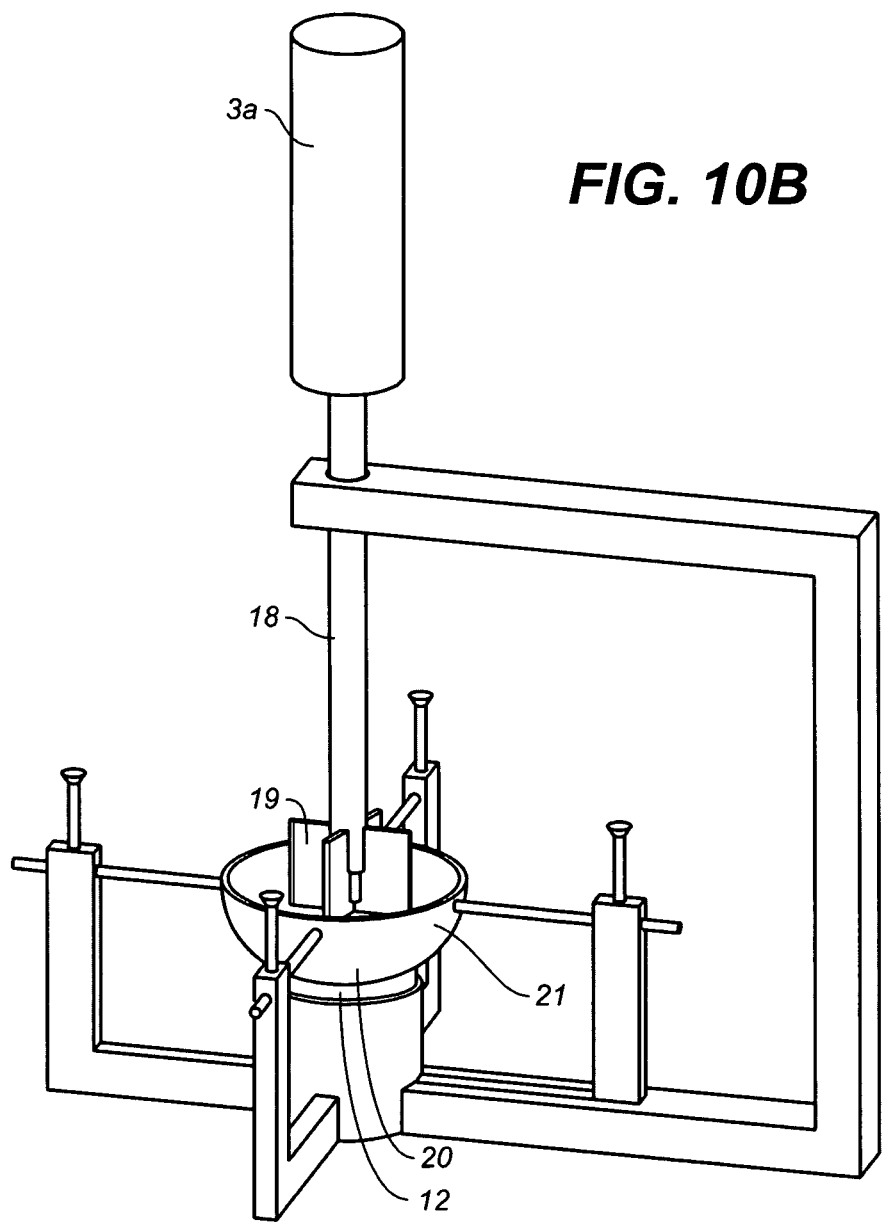
FIG. 10B is an upper left rear view thereof with the femoral head harvester reamer in a "down" position, as when reaming the central portion of a femoral head allograft.

In FIG. 9A there is shown a schematic perspective view of an allograft femoral head 21. In FIG. 9B, the femoral head allograft is shown as placed on the APS in femoral head preparation mode. Once the graft has been placed in the APS as shown in FIG. 9B, a standard bone saw is used to perform a horizontal cut on the non-articular portion of the graft, essentially removing the femoral neck. Once this has been performed, the femoral head allograft reamer of the desired size is mounted on the APS, as shown in FIG. 10A. The femoral head reamer is then lowered onto the femoral head to the desired depth based on the adjustment of the piston 12, thereby creating a uniform femoral head thickness for the graft and a predetermined cylindrical inner diameter for the graft as shown in FIG. 10C.

Figure 11C:
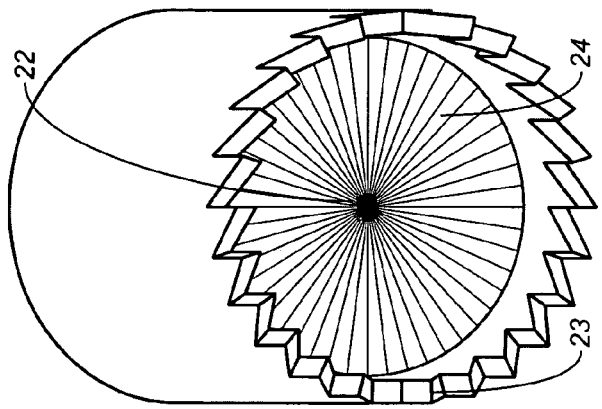
FIG. 11C is a lower perspective view thereof showing both the outer reamer cutting blades and the inner planing reamer surface.
Figure 11B:
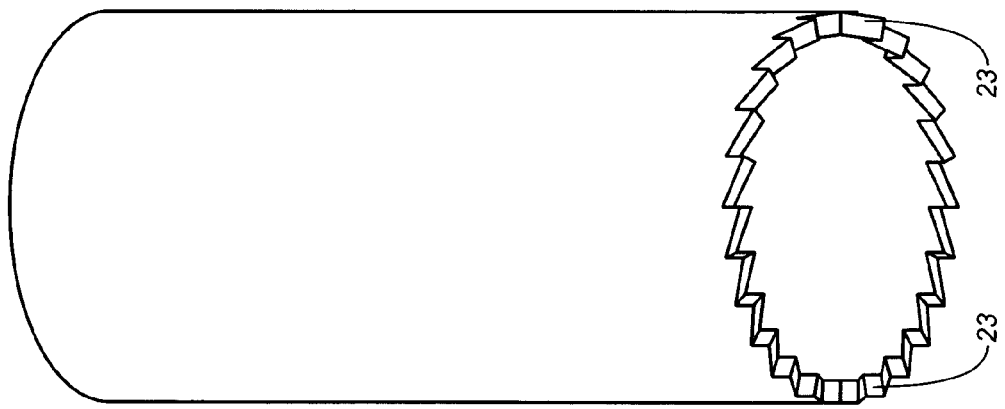
FIG. 11B is a lower perspective view thereof.
Figure 11A:
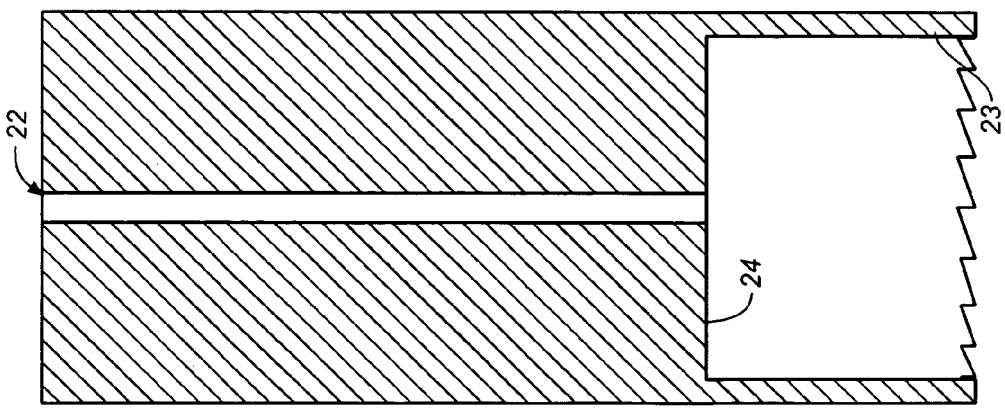
FIG. 11A is a cross-sectional side view in elevation showing a cylindrical recipient inner femoral head reamer.

FIGS. 11A-11C show the cylindrical recipient inner femoral head reamer used to prepare the recipient head. FIG. 11A is a cross-sectional side view in elevation of the reamer with its central cylindrical aperture 22 to accommodate a metal guide-pin, the circumferential inner reamer cutting blade 23 disposed on its inferior aspect, and a recessed inner planing reamer surface 24.

Figure 12A:
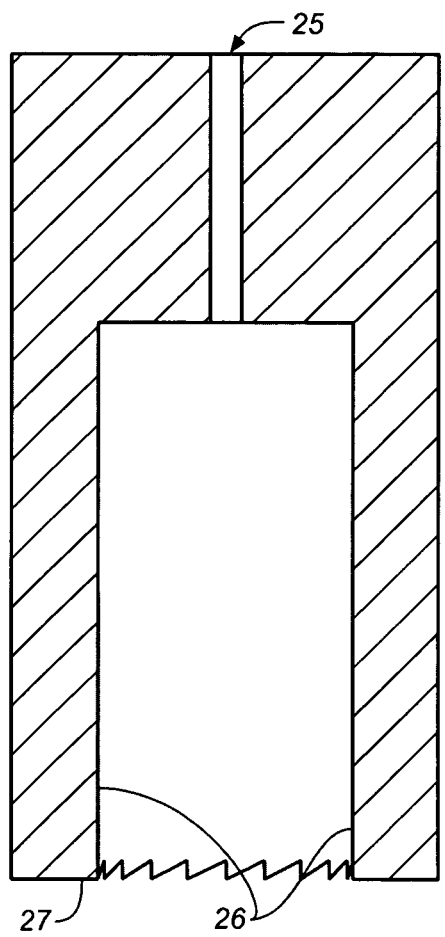
FIG. 12A is a cross-sectional side view in elevation of a cylindrical recipient outer femoral head reamer.

In FIGS. 12A and B there is shown a cross-sectional schematic diagram and a perspective view, respectively, of a cylindrical recipient outer femoral head reamer. These views show the inner diameter of the reamer matched to the outer diameter of the cylindrical recipient inner femoral head reamer from FIGS. 11A-11C. This reamer contains a central cylindrical aperture 25, an inner cylindrical cavity 26, and a circumferential cutting blade 27 disposed at its inferior aspect, preferably comprising a plurality of saw teeth.

Figure 12B:
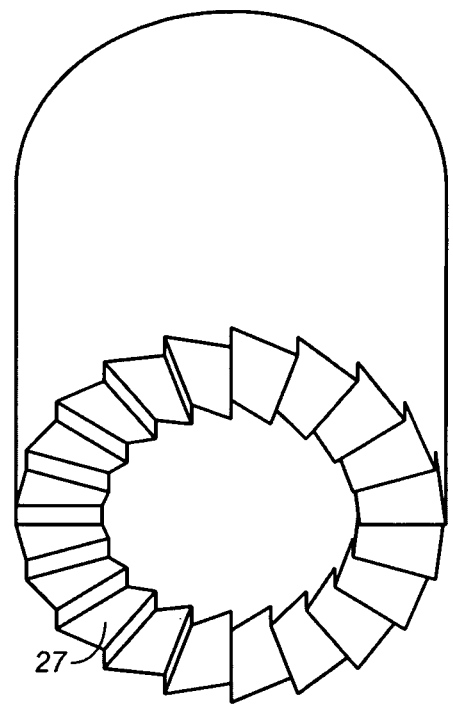
FIG. 12B is a lower perspective view thereof, showing the outer saw teeth.

FIGS. 13A and 13B show the combination cylindrical recipient femoral head reamer comprising the inner and outer recipient femoral head reamers shown in FIGS. 11 and 12.

FIG. 13A is a cross-sectional diagram of the combination reamer with its central cylindrical aperture composed of the apertures of the inner and outer reamers and the fit between the outer circumference of the inner reamer and the inner circumference of the outer reamer. As will be appreciated from this view, when the cylindrical recipient femoral head reamer is inserted into the inner cylindrical cavity 26 of the outer recipient femoral head reamer, the tips of the cutting blades of each inner and outer reamer 23, 27, respectively, are generally coplanar and thus create a substantially coplanar cut surface (as will be seen by reference to FIG. 14D).

Figure 14A:
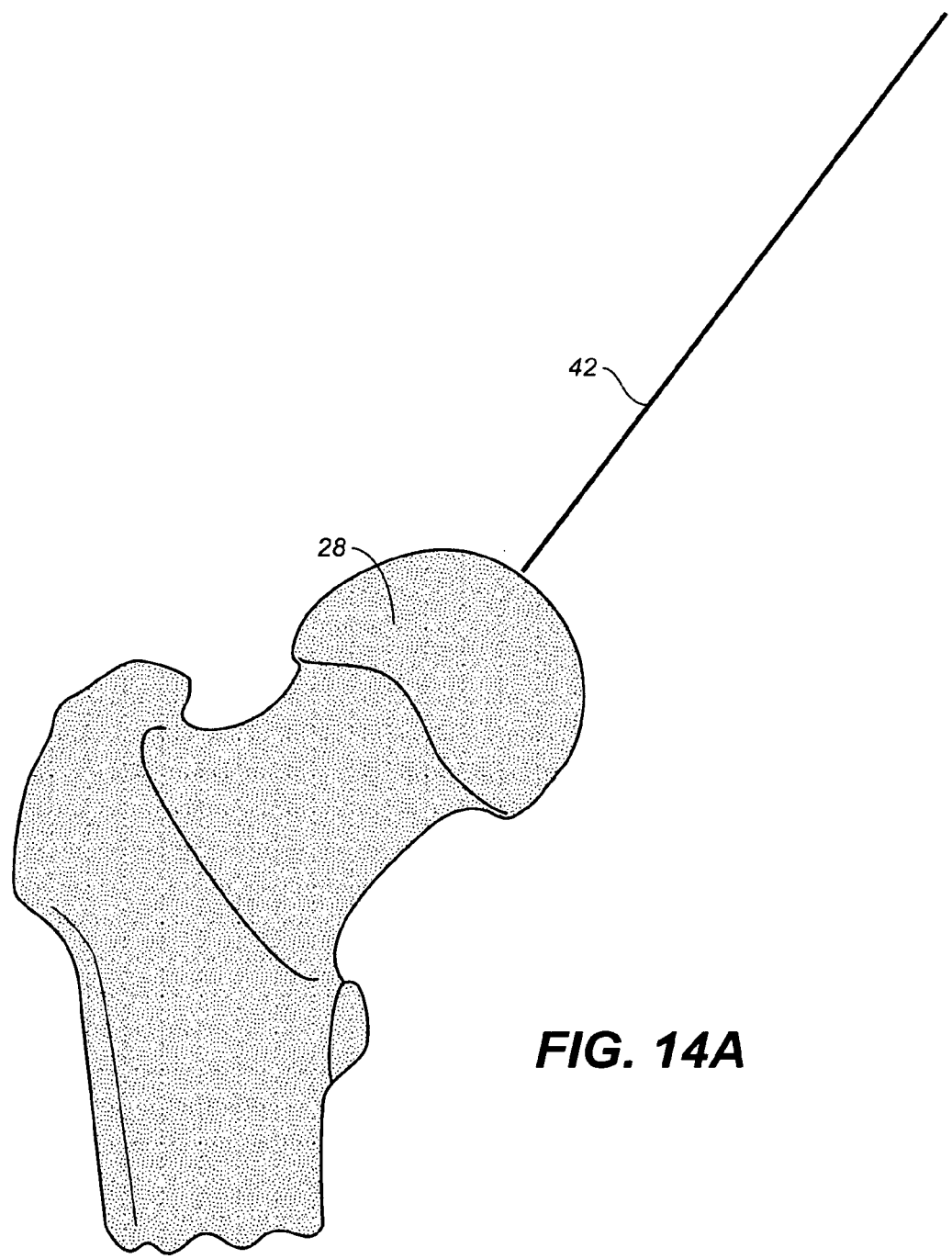
FIG. 14A is a schematic perspective view of a recipient femoral head with a centrally placed guidepin.
Figure 14B:
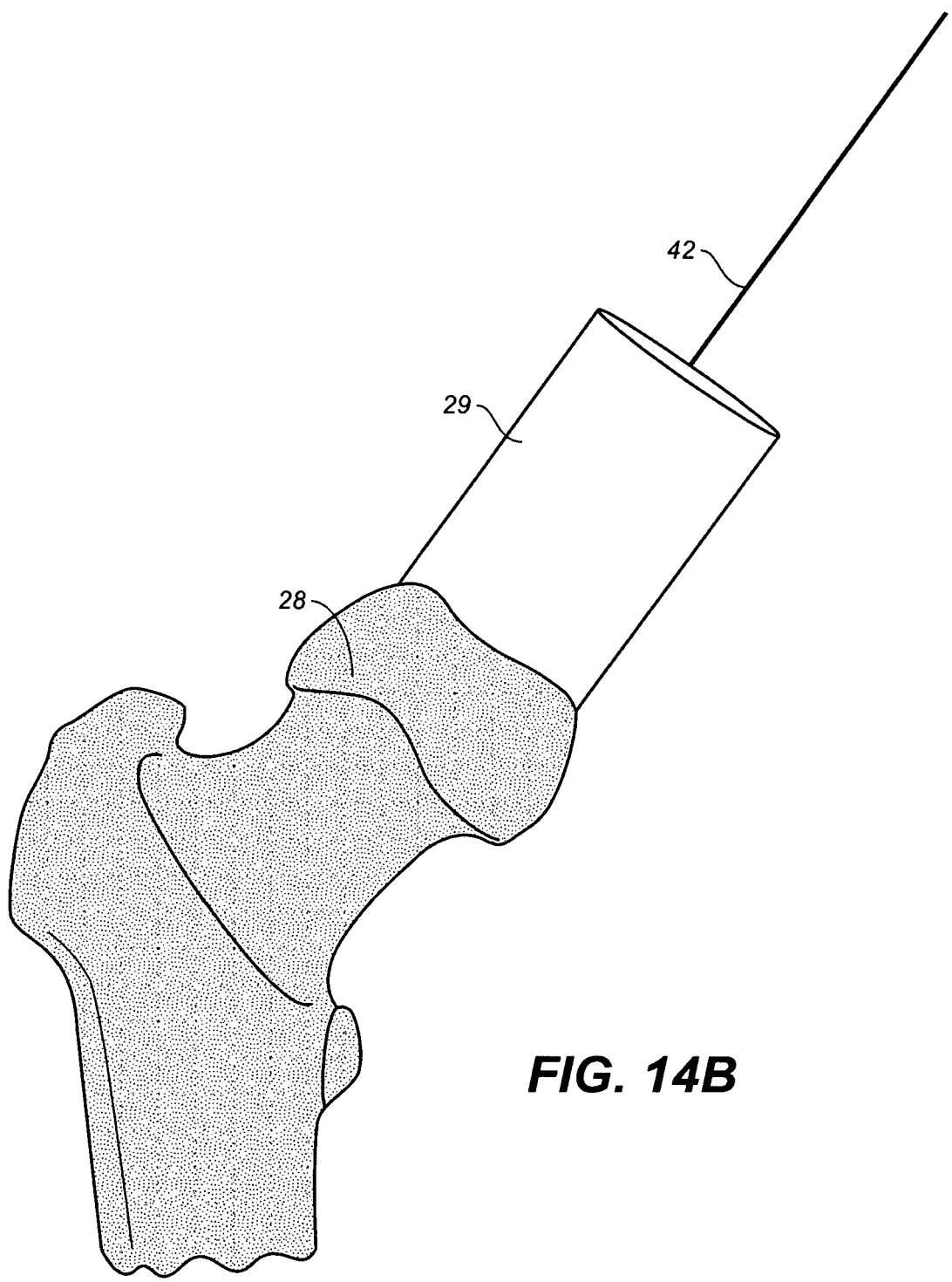
FIG. 14B is the same view as that of FIG. 14A after passage of the cylindrical recipient inner femoral head reamer.

FIG. 14A is a perspective view of the recipient femoral head with a central guidepin 42 that is placed in the head 28 in accordance with mechanical guides or computer navigation systems that are widely available to those skilled in the art of hip surgery. Subsequent to placement of the guidepin as shown in FIG. 14B, the cylindrical recipient inner femoral head reamer 29 is passed over the guide pin 42 to the desired depth based on markings outside the reamer or through longitudinal slots cut into the reamer.

Figure 14C:
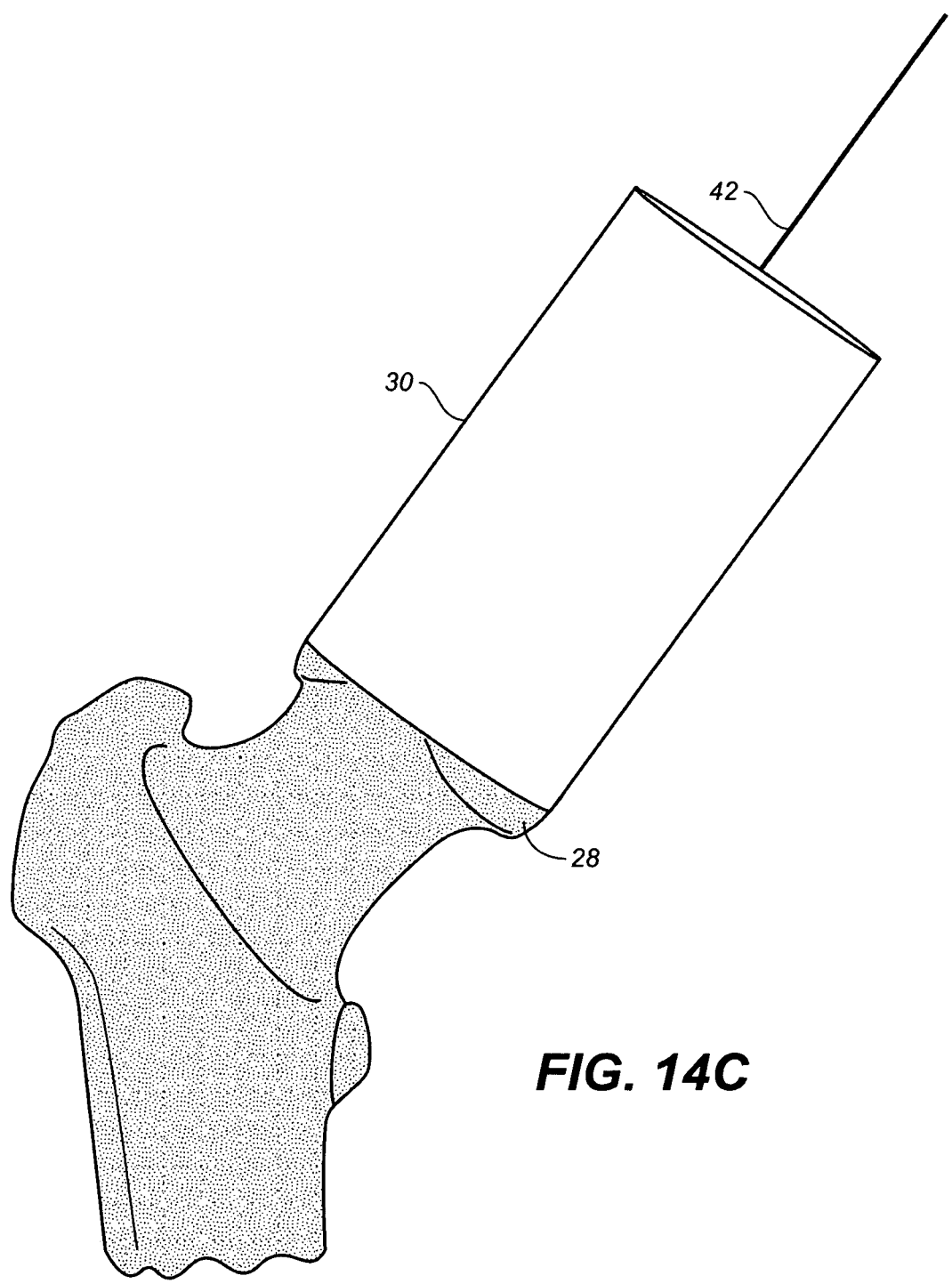
FIG. 14C is the same view thereof, showing the recipient femoral head after passage of the recipient outer femoral head reamer.
Figure 14D:
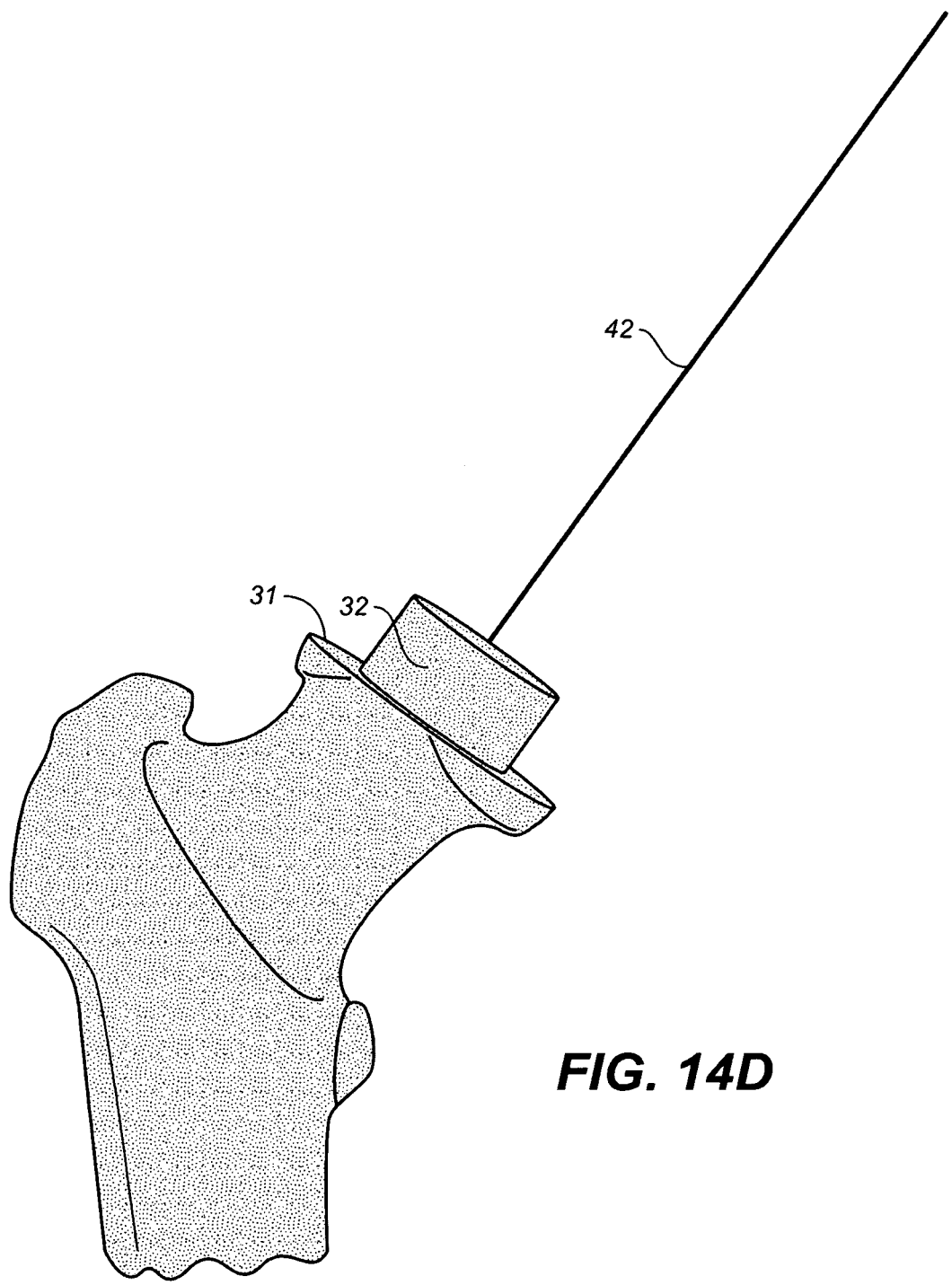
FIG. 14D is the same view thereof showing the recipient femoral head after a reaming is process is completed and the recipient femoral head reamers removed.

Next, as shown in FIG. 14C, the cylindrical (or cannulated) recipient outer femoral head reamer 30 is passed over the guidepin and over the inner reamer (29 in FIG. 14B) until it is fully seated on the inner reamer as shown in FIGS. 13A-13B. Once both recipient reamers are removed the final preparation of the recipient femoral head 32 is shown in FIG. 14D as a flat surface on the periphery of the neck 31 with a cylindrical bony platform of the femoral head 32 to press fit into the femoral head allograft such that the diameter of the bone platform is 0 to 1 mm larger than the allograft head cylindrical inner diameter as shown in FIG. 10C. Various size combinations in 1 mm increments between 30 mm and 60 mm of the inner and outer recipient femoral head reamers can be manufactured to match (exactly or nearly exactly for all practical purposes) all possible inner diameters of the prepared femoral head allograft. By exactly or nearly exactly matching the outer diameter of the femoral head remnant to the inner diameter of the graft, initial press-fit stability will be achieved with the femoral head allograft, minimizing the need for additional hardware.

Figure 15:
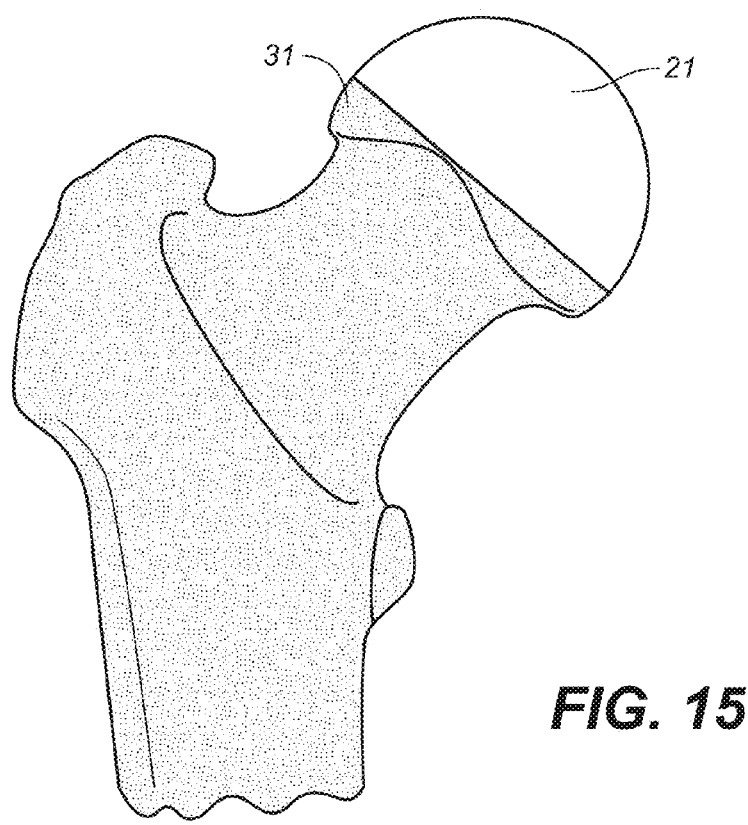
FIG. 15 is a schematic perspective view showing the recipient femoral head after placement of the femoral head allograft.

FIG. 15 shows a perspective view of the final femoral head allograft 21 mounted onto the flat peripheral surface of the recipient femoral head 32 with a press-fit fixation. Additional fixation with resorbable or metal screws can be achieved as necessary to secure the graft to the recipient femoral head.

Figure 16A:
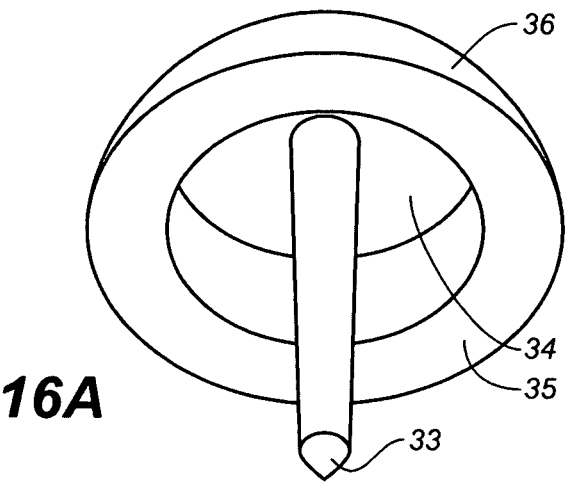
FIGS. 16A and 16B are lower perspective views showing a metal or ceramic resurfacing femoral component as an alternative embodiment of the invention used to cap the prepared recipient femoral head.
Figure 16B:
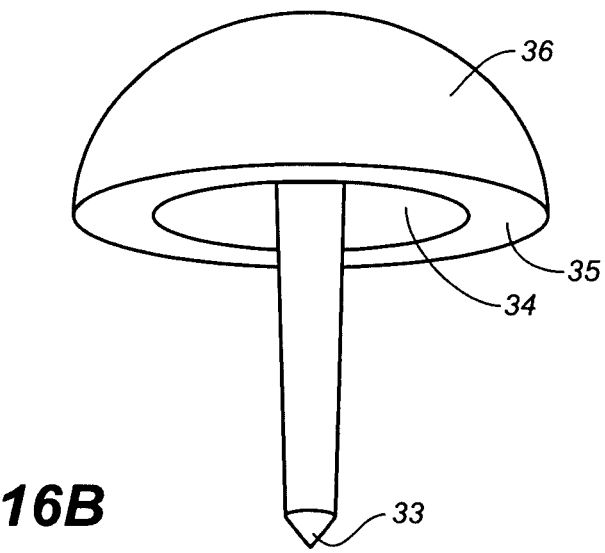

FIGS. 16A and 16B show an alternative apparatus suitable for capping the recipient femoral head. This apparatus comprises a metal or ceramic femoral resurfacing implant, which includes a central stem 31, an inner cavity 34, a normalized periphery 35, and an outer hemispherical surface 36. The normalized periphery 35 can achieve axial compression onto the native femoral head bone surface 31 after removal of both the inner 29 and outer 30 recipient femoral head reamers as shown in FIG. 14D.

Figure 17:
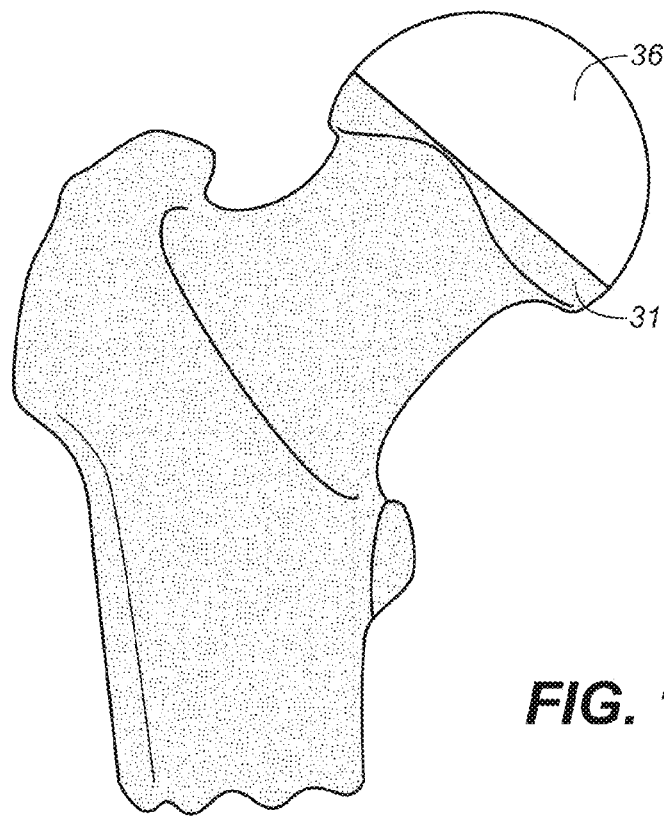
FIG. 17 is a schematic perspective view showing the recipient femoral head after placement of the metal or ceramic resurfacing femoral head implant shown in FIGS. 16A and 16B.

FIG. 17 is a perspective view of the recipient femoral head with the metal or ceramic resurfacing implant showing the hemispherical outer surface of the implant 36 resting on the normally (perpendicularly) cut recipient femoral head periphery 31.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. An apparatus for preparing and reconstructing the human acetabulum, femoral head, or both, using tissue engineered osteochondral constructs and/or an osteochondral allograft transplant, said apparatus comprising:
   a base for placement of said apparatus on a generally flat surface;
   a support disposed generally vertically from said base;
   an arm attached to or integral with said support;
   a motorized reamer secured on said arm and having a vertically disposed drive shaft;
   a cutting tool mounted on said drive shaft, wherein said cutting tool is a cup-shaped reverse hemisphere reamer having cutting elements disposed on its inner surface for removing excess bone and sculpting the acetabular allograft or osteochondral construct to the precise size and thickness needed for the procedure;
   a stabilization platform disposed immediately under said cutting tool for placement of an allograft or osteochondral construct; and
   workpiece holding apparatus for securing the allograft or osetochondral construct in position on said platform; said workpiece holding apparatus including a plurality of horizontally oriented stabilization rods disposed around said stabilization platform for holding a femoral head at its peripheral surface during a head reaming process, such that the entire surface of an acetabular graft or femoral head can be prepared.

2. An apparatus for preparing and reconstructing the human acetabulum, femoral head, or both, using tissue engineered osteochondral constructs and/or an osteochondral allograft transplant, said apparatus comprising:
   a base for placement of said apparatus on a generally flat surface;
   a support disposed generally vertically from said base;
   an arm attached to or integral with said support;
   a motorized reamer secured on said arm and having a vertically disposed drive shaft;
   a cutting tool mounted on said drive shaft;
   a stabilization platform disposed immediately under said cutting tool for placement of an allograft or osteochondral construct; and
   workpiece holding apparatus for securing the allograft or osetochondral construct in position on said platform; said workpiece holding apparatus including a plurality of horizontally oriented stabilization rods disposed around said stabilization platform for holding a femoral head at its peripheral surface during a head reaming process, such that the entire surface of an acetabular graft or femoral head can be prepared; and
   a height-adjustable piston on which said acetabular platform is mounted for adjusting the height of said platform to control the final polar thickness of the acetabular graft.

3. An apparatus for preparing and reconstructing the human acetabulum, femoral head, or both, using tissue engineered osteochondral constructs and/or an osteochondral allograft transplant, said apparatus comprising:
   a base for placement of said apparatus on a generally flat surface;
   a support disposed generally vertically from said base;
   an arm attached to or integral with said support;
   a motorized reamer secured on said arm and having a vertically disposed drive shaft;
   a cutting tool mounted on said drive shaft;
   a stabilization platform disposed immediately under said cutting tool for placement of an allograft or osteochondral construct; and
   workpiece holding apparatus for securing the allograft or osetochondral construct in position on said platform; said workpiece holding apparatus including a plurality of horizontally oriented stabilization rods disposed around said stabilization platform for holding a femoral head at its peripheral surface during a head reaming process, such that the entire surface of an acetabular graft or femoral head can be prepared;
   wherein said platform is a femoral head platform, said motorized reamer is a femoral head allograft reamer, and said cutting tool is a cruciate head reamer having blades with cutting edges perpendicular to said drive shaft.

4. The apparatus of claim 3, wherein said cruciate head reamer includes a plurality of blades.

5. The apparatus of claim 3, wherein said femoral head platform is selected from a set of interchangeable cup-shaped platforms having varying inner radii of curvature so as to accommodate femoral head allografts of varying sizes and shapes.

6. The apparatus of claim 3, further including a height-adjustable piston on which said femoral head platform is mounted.

7. An apparatus for preparing and reconstructing the human acetabulum, femoral head, or both, using tissue engineered osteochondral constructs and/or an osteochondral allograft transplant, said apparatus comprising:
   a base for placement of said apparatus on a generally flat surface;
   a support disposed generally vertically from said base;
   an arm attached to or integral with said support;
   a motorized reamer secured on said arm and having a vertically disposed drive shaft;

a cutting tool mounted on said drive shaft, wherein said cutting tool is a reverse hemispherical reamer for precisely machining the nonarticular side of an acetabular graft to a given diameter and to allow a thickness of between 5 and 10 mm for the graft;

a stabilization platform disposed immediately under said cutting tool for placement of an allograft or osteochondral construct; and workpiece holding apparatus for securing the allograft or osetochondral construct in position on said platform; said workpiece holding apparatus including a plurality of horizontally oriented stabilization rods disposed around said stabilization platform for holding a femoral head at its peripheral surface during a head reaming process, such that the entire surface of an acetabular graft or femoral head can be prepared.

8. An apparatus for preparing and reconstructing the human acetabulum, femoral head, or both, using tissue engineered osteochondral constructs and/or an osteochondral allograft transplant, said apparatus comprising:

a base for placement of said apparatus on a generally flat surface;

a support disposed generally vertically from said base;

an arm attached to or integral with said support;

a motorized reamer secured on said arm and having a vertically disposed drive shaft;

a cutting tool mounted on said drive shaft;

a stabilization platform disposed immediately under said cutting tool for placement of an allograft or osteochondral construct; and workpiece holding apparatus for securing the allograft or osetochondral construct in position on said platform; said workpiece holding apparatus including a plurality of horizontally oriented stabilization rods disposed around said stabilization platform for holding a femoral head at its peripheral surface during a head reaming process, such that the entire surface of an acetabular graft or femoral head can be prepared;

wherein said stabilization platform is interchangeable between a convex acetabular platform that allows secure stabilization of an acetabular graft with its articular surface exposed for cutting by said cutting tool, and a concave femoral head platform that allows secure stabilization of the graft femoral head with its articular surface resting on the concave femoral platform, each of said grafts being held in place with said workpiece holding apparatus.

9. An apparatus for preparing and reconstructing the human acetabulum, femoral head, or both, using tissue engineered osteochondral constructs and/or an osteochondral allograft transplant, said apparatus comprising:

a base for placement of said apparatus on a generally flat surface;

a support disposed generally vertically from said base;

an arm attached to or integral with said support;

a motorized reamer secured on said arm and having a vertically disposed drive shaft;

a cutting tool mounted on said drive shaft;

a stabilization platform disposed immediately under said cutting tool for placement of an allograft or osteochondral construct; and workpiece holding apparatus for securing the allograft or osetochondral construct in position on said platform; said workpiece holding apparatus including a plurality of horizontally oriented stabilization rods disposed around said stabilization platform for holding a femoral head at its peripheral surface during a head reaming process, such that the entire surface of an acetabular graft or femoral head can be prepared; and recipient femoral head preparation tools for prepare a recipient femoral head in line with a guidewire and to prepare a peripherally recessed femoral head with a centrally raised cylindrical platform, said recipient femoral head preparation tools comprising a cylindrical recipient inner femoral head reamer having a circumferential inner reamer cutting blade, a recessed inner planing reaming surface, and a central cylindrical aperture for accommodating a metal guide-pin; and a cylindrical recipient outer femoral head reamer having a circumferential outer reamer cutting blade disposed on its inferior aspect, an inner cylindrical cavity of sufficient diameter to accommodate said cylindrical recipient inner femoral head reamer, and a central cylindrical aperture, such that when said recipient inner femoral head reamer is inserted into the inner cylindrical cavity of said recipient outer femoral head reamer, the central cylindrical apertures are aligned and said inner reamer cutting blade and said outer reamer cutting blade are generally coplanar.

\* \* \* \* \*